United States Patent
Kane et al.

(10) Patent No.: US 11,571,151 B2
(45) Date of Patent: Feb. 7, 2023

(54) IMPLANTABLE CHEMICAL SENSOR WITH STAGED ACTIVATION

(71) Applicant: Cardiac Pacemakers, Inc., St. Paul, MN (US)

(72) Inventors: Michael John Kane, St. Paul, MN (US); Yingbo Li, Shanghai (CN)

(73) Assignee: Cardiac Pacemakers, Inc., St. Paul, MN (US)

( * ) Notice: Subject to any disclaimer, the term of this patent is extended or adjusted under 35 U.S.C. 154(b) by 514 days.

(21) Appl. No.: 16/106,623

(22) Filed: Aug. 21, 2018

(65) Prior Publication Data

US 2019/0059792 A1    Feb. 28, 2019

(30) Foreign Application Priority Data

Aug. 23, 2017  (CN) .......................... 201710730979.1

(51) Int. Cl.
*A61B 5/1473*    (2006.01)
*A61B 5/145*    (2006.01)
(Continued)

(52) U.S. Cl.
CPC .......... *A61B 5/1473* (2013.01); *A61B 5/0031* (2013.01); *A61B 5/1451* (2013.01);
(Continued)

(58) Field of Classification Search
None
See application file for complete search history.

(56) References Cited

U.S. PATENT DOCUMENTS

| 556,421 A | 3/1896 | Judge |
| 4,200,110 A | 4/1980 | Peterson et al. |

(Continued)

FOREIGN PATENT DOCUMENTS

| EP | 3440999 | 2/2019 |
| EP | 3492014 | 6/2019 |

(Continued)

OTHER PUBLICATIONS

Communication Pursuant to Article 94(3) EPC for European Patent Application No. 18207668.7 dated Aug. 4, 2020 (5 pages).

(Continued)

*Primary Examiner* — Jacqueline Cheng
*Assistant Examiner* — Jairo H Portillo
(74) *Attorney, Agent, or Firm* — Pauly, DeVries, Smith & Deffner LLC

(57) ABSTRACT

Embodiments herein include implantable medical devices including chemical sensors with bioerodible masking layers to allow for staged activation of the sensors. In an embodiment, an implantable medical device includes a substrate defining wells and a first chemical sensor and a second chemical sensor disposed within separate wells of the substrate. The first chemical sensor and the second chemical sensor can be configured to detect one or more analytes. The device can include a first bioerodible masking layer disposed over the second chemical sensor, sealing off the second chemical sensor. The device can further include a protective planarization layer disposed over at least one of the first chemical sensor and the second chemical sensor such that the outermost surface of the medical device over the first sensor is flush with the outermost surface of the medical device over the second sensor. Other embodiments are also included herein.

14 Claims, 5 Drawing Sheets

(51) Int. Cl.
*A61B 5/00* (2006.01)
*A61B 5/1486* (2006.01)
*A61L 31/08* (2006.01)

(52) U.S. Cl.
CPC ...... *A61B 5/14503* (2013.01); *A61B 5/14532* (2013.01); *A61B 5/14546* (2013.01); *A61B 5/14865* (2013.01); *A61B 5/686* (2013.01); *A61L 31/08* (2013.01); *A61B 5/4836* (2013.01); *A61L 2300/608* (2013.01)

(56) References Cited

U.S. PATENT DOCUMENTS

| | | | |
|---|---|---|---|
| 4,321,057 A | 3/1982 | Buckles | |
| 4,344,438 A | 8/1982 | Schultz et al. | |
| 4,399,099 A | 8/1983 | Buckles | |
| 4,680,268 A | 7/1987 | Clark | |
| 4,704,029 A | 11/1987 | Van Heuvelen | |
| 4,721,677 A | 1/1988 | Clark | |
| 4,750,494 A | 6/1988 | King | |
| 4,750,495 A | 6/1988 | Moore et al. | |
| 4,890,621 A | 1/1990 | Hakky | |
| 4,903,701 A | 2/1990 | Moore | |
| 4,981,779 A | 1/1991 | Wagner | |
| 5,001,054 A | 3/1991 | Wagner | |
| 5,040,533 A | 8/1991 | Fearnot | |
| 5,090,326 A | 2/1992 | Altenau et al. | |
| 5,209,231 A | 5/1993 | Cote et al. | |
| 5,267,151 A | 11/1993 | Ham et al. | |
| 5,275,171 A | 1/1994 | Barcel | |
| 5,312,439 A | 5/1994 | Loeb | |
| 5,312,454 A | 5/1994 | Roline et al. | |
| 5,330,718 A | 7/1994 | Hui et al. | |
| 5,333,609 A | 8/1994 | Bedingham et al. | |
| 5,342,406 A | 8/1994 | Thompson | |
| 5,342,789 A | 8/1994 | Chick et al. | |
| 5,355,880 A | 10/1994 | Thomas et al. | |
| 5,378,432 A | 1/1995 | Bankert et al. | |
| 5,419,329 A | 5/1995 | Smith et al. | |
| 5,457,535 A | 10/1995 | Schmidtke et al. | |
| 5,476,434 A | 12/1995 | Kalb et al. | |
| 5,553,616 A | 9/1996 | Ham et al. | |
| 5,556,421 A | 9/1996 | Prutchi et al. | |
| 5,560,356 A | 10/1996 | Peyman | |
| 5,605,152 A | 2/1997 | Slate et al. | |
| 5,607,644 A | 3/1997 | Olstein et al. | |
| 5,660,163 A | 8/1997 | Schulman et al. | |
| 5,728,281 A | 3/1998 | Holmstrom et al. | |
| 5,730,125 A | 3/1998 | Prutchi et al. | |
| 5,741,211 A | 4/1998 | Renirie et al. | |
| 5,797,898 A | 8/1998 | Santini et al. | |
| 5,830,138 A | 11/1998 | Wilson | |
| 5,833,603 A | 11/1998 | Kovacs et al. | |
| 5,854,078 A | 12/1998 | Asher | |
| 5,871,442 A | 2/1999 | Madarasz et al. | |
| 5,902,326 A | 5/1999 | Lessar et al. | |
| 5,958,782 A | 9/1999 | Bentsen et al. | |
| 5,995,860 A | 11/1999 | Sun et al. | |
| 6,002,954 A | 12/1999 | Van Antwerp et al. | |
| 6,011,984 A | 1/2000 | Van Antwerp et al. | |
| 6,040,194 A | 3/2000 | Chick et al. | |
| 6,049,727 A | 4/2000 | Crothall | |
| 6,070,093 A | 5/2000 | Oosta et al. | |
| 6,097,139 A | 8/2000 | Tuck et al. | |
| 6,122,536 A | 9/2000 | Sun et al. | |
| 6,123,861 A | 9/2000 | Santini et al. | |
| 6,125,290 A | 9/2000 | Miesel | |
| 6,125,291 A | 9/2000 | Miesel et al. | |
| 6,134,459 A | 10/2000 | Roberts et al. | |
| 6,144,866 A | 11/2000 | Miesel et al. | |
| 6,163,714 A | 12/2000 | Stanley et al. | |
| 6,175,642 B1 | 1/2001 | Gobbi et al. | |
| 6,187,599 B1 | 2/2001 | Asher et al. | |
| 6,216,022 B1 | 4/2001 | Tyrrell et al. | |
| 6,219,137 B1 | 4/2001 | Vo-Dinh | |
| 6,232,130 B1 | 5/2001 | Wolf | |
| 6,236,870 B1 | 5/2001 | Madarasz et al. | |
| 6,256,522 B1 | 7/2001 | Schultz | |
| 6,267,724 B1 | 7/2001 | Taylor et al. | |
| 6,268,161 B1 | 7/2001 | Han et al. | |
| 6,277,627 B1 | 8/2001 | Hellinga | |
| 6,304,766 B1 | 10/2001 | Colvin, Jr. | |
| 6,330,464 B1 | 12/2001 | Colvin et al. | |
| 6,343,223 B1 | 1/2002 | Chin et al. | |
| 6,344,340 B1 | 2/2002 | Dibner et al. | |
| 6,368,274 B1 | 4/2002 | Van Antwerp et al. | |
| 6,383,767 B1 | 5/2002 | Polak | |
| 6,438,397 B1 | 8/2002 | Bosquet et al. | |
| 6,442,409 B1 | 8/2002 | Peyman | |
| 6,454,710 B1 | 9/2002 | Ballerstadt et al. | |
| 6,466,821 B1 | 10/2002 | Pianca et al. | |
| 6,491,639 B1 | 12/2002 | Turcott | |
| 6,491,666 B1 | 12/2002 | Santini, Jr. et al. | |
| 6,505,059 B1 | 1/2003 | Kollias et al. | |
| 6,521,446 B2 | 2/2003 | Hellinga | |
| 6,527,762 B1 | 3/2003 | Santini, Jr. et al. | |
| 6,544,800 B2 | 4/2003 | Asher | |
| 6,551,838 B2 | 4/2003 | Santini, Jr. et al. | |
| 6,579,690 B1 | 6/2003 | Bonnecaze et al. | |
| 6,594,092 B2 | 7/2003 | Von et al. | |
| 6,594,510 B2 | 7/2003 | Madarasz et al. | |
| 6,602,521 B1 * | 8/2003 | Ting | A61J 3/10 424/464 |
| 6,625,479 B1 | 9/2003 | Weber et al. | |
| 6,666,821 B2 | 12/2003 | Keimel et al. | |
| 6,671,527 B2 | 12/2003 | Petersson et al. | |
| 6,673,596 B1 | 1/2004 | Sayler et al. | |
| 6,682,938 B1 | 1/2004 | Satcher, Jr. et al. | |
| 6,694,158 B2 | 2/2004 | Polak | |
| 6,711,423 B2 | 3/2004 | Colvin | |
| 6,731,976 B2 | 5/2004 | Penn et al. | |
| RE38,525 E | 6/2004 | Stanley et al. | |
| 6,766,183 B2 | 7/2004 | Walsh | |
| 6,771,993 B2 | 8/2004 | Rule et al. | |
| 6,800,451 B2 | 10/2004 | Daniloff et al. | |
| 6,804,544 B2 | 10/2004 | Van Antwerp et al. | |
| 6,814,490 B1 | 11/2004 | Suhm et al. | |
| 6,815,162 B2 | 11/2004 | Boukherroub et al. | |
| 6,835,553 B2 | 12/2004 | Han et al. | |
| 6,855,556 B2 | 2/2005 | Amiss et al. | |
| 6,875,208 B2 | 4/2005 | Santini, Jr. et al. | |
| 6,885,881 B2 | 4/2005 | Leonhardt | |
| 6,885,883 B2 | 4/2005 | Parris et al. | |
| 6,893,545 B2 | 5/2005 | Gotoh et al. | |
| 6,912,078 B2 | 6/2005 | Kudrle et al. | |
| 6,918,873 B1 | 7/2005 | Millar et al. | |
| 6,928,325 B2 | 8/2005 | Zhu et al. | |
| 6,937,900 B1 | 8/2005 | Pianca et al. | |
| 6,944,488 B2 | 9/2005 | Roberts | |
| 6,952,603 B2 | 10/2005 | Gerber et al. | |
| 6,957,094 B2 | 10/2005 | Chance et al. | |
| 6,976,982 B2 | 12/2005 | Santini, Jr. et al. | |
| 6,978,182 B2 | 12/2005 | Mazar et al. | |
| 7,016,714 B2 | 3/2006 | Colvin, Jr. et al. | |
| 7,039,446 B2 | 5/2006 | Ruchti et al. | |
| 7,070,590 B1 | 7/2006 | Santini, Jr. et al. | |
| 7,107,086 B2 | 9/2006 | Reihl et al. | |
| 7,133,710 B2 | 11/2006 | Acosta et al. | |
| 7,134,999 B2 | 11/2006 | Brauker et al. | |
| 7,164,948 B2 | 1/2007 | Struble et al. | |
| 7,166,871 B2 | 1/2007 | Erchak | |
| 7,174,212 B1 | 2/2007 | Klehn et al. | |
| 7,225,024 B2 | 5/2007 | Zhu et al. | |
| 7,236,821 B2 | 6/2007 | Cates et al. | |
| 7,410,616 B2 | 8/2008 | Santini, Jr. et al. | |
| 7,447,533 B1 | 11/2008 | Fang et al. | |
| 7,449,246 B2 | 11/2008 | Kim et al. | |
| 7,450,980 B2 | 11/2008 | Kawanishi | |
| 7,471,290 B2 | 12/2008 | Wang et al. | |
| 7,577,470 B2 | 8/2009 | Shah et al. | |
| 7,632,234 B2 | 12/2009 | Manda et al. | |
| 7,633,356 B2 | 12/2009 | Hamet et al. | |
| 7,686,762 B1 | 3/2010 | Najafi et al. | |
| 7,761,130 B2 | 7/2010 | Simpson et al. | |

(56) References Cited

U.S. PATENT DOCUMENTS

| | | |
|---|---|---|
| 7,805,174 B2 | 9/2010 | Carpenter et al. |
| 7,809,441 B2 | 10/2010 | Kane et al. |
| 7,829,147 B2 | 11/2010 | Aitken et al. |
| 7,890,171 B2 | 2/2011 | Zhu et al. |
| 7,894,884 B2 | 2/2011 | Song et al. |
| 8,126,554 B2 | 2/2012 | Kane et al. |
| 8,131,364 B2 | 3/2012 | Zhu et al. |
| 8,141,489 B2 | 3/2012 | Belanger et al. |
| 8,160,670 B2 | 4/2012 | Ouyang et al. |
| 8,165,840 B2 | 4/2012 | Hatlestad et al. |
| 8,257,067 B2 | 9/2012 | Fukui et al. |
| 8,290,592 B2 | 10/2012 | Michael et al. |
| 8,303,511 B2 | 11/2012 | Eigler et al. |
| 8,378,453 B2 | 2/2013 | Fedorov et al. |
| 8,414,489 B2 | 4/2013 | Shah et al. |
| 8,435,604 B2 | 5/2013 | Aitken et al. |
| 8,527,067 B2 | 9/2013 | De Kock et al. |
| 8,571,659 B2 | 10/2013 | Kane et al. |
| 8,636,884 B2 | 1/2014 | Feldman et al. |
| 8,710,625 B2 | 4/2014 | Fedorov et al. |
| 8,765,060 B2 | 7/2014 | Buhlmann et al. |
| 8,827,899 B2 | 9/2014 | Farr et al. |
| 9,101,277 B2 | 8/2015 | Doerr |
| 9,326,707 B2 | 5/2016 | McGarraugh |
| 9,357,968 B2 | 6/2016 | Hauer et al. |
| 9,399,076 B2 | 7/2016 | Yu et al. |
| 9,693,714 B2 | 7/2017 | Dehennis et al. |
| 10,194,808 B1 | 2/2019 | Thompson et al. |
| 10,667,745 B2 | 6/2020 | Anker et al. |
| 10,952,621 B2 | 3/2021 | Kane et al. |
| 11,089,983 B2 | 8/2021 | Li et al. |
| 11,129,557 B2 | 9/2021 | Li et al. |
| 11,439,304 B2 | 9/2022 | Stahmann et al. |
| 2002/0016535 A1 | 2/2002 | Martin et al. |
| 2002/0026108 A1 | 2/2002 | Colvin |
| 2002/0033260 A1 | 3/2002 | Lungwitz et al. |
| 2002/0033454 A1 | 3/2002 | Cheng et al. |
| 2002/0035317 A1 | 3/2002 | Cheng et al. |
| 2002/0095075 A1 | 7/2002 | Madarasz et al. |
| 2002/0127626 A1 | 9/2002 | Daniloff et al. |
| 2002/0151812 A1 | 10/2002 | Scheiner et al. |
| 2003/0100040 A1 | 5/2003 | Bonnecaze et al. |
| 2003/0114735 A1* | 6/2003 | Silver ................ A61B 5/14865 600/300 |
| 2003/0191376 A1 | 10/2003 | Samuels et al. |
| 2003/0208113 A1 | 11/2003 | Mault et al. |
| 2004/0023317 A1 | 2/2004 | Motamedi et al. |
| 2004/0030365 A1 | 2/2004 | Rubin |
| 2004/0059206 A1 | 3/2004 | Braig et al. |
| 2004/0073100 A1 | 4/2004 | Ballerstadt et al. |
| 2004/0087842 A1 | 5/2004 | Lakowicz et al. |
| 2004/0100376 A1 | 5/2004 | Lye et al. |
| 2004/0106953 A1 | 6/2004 | Yomtov et al. |
| 2004/0132172 A1 | 7/2004 | Cunningham et al. |
| 2004/0133079 A1 | 7/2004 | Mazar et al. |
| 2004/0147034 A1 | 7/2004 | Gore et al. |
| 2004/0161853 A1 | 8/2004 | Yang et al. |
| 2004/0176669 A1 | 9/2004 | Colvin, Jr. |
| 2004/0180379 A1 | 9/2004 | Van Duyne et al. |
| 2004/0180391 A1 | 9/2004 | Gratzl et al. |
| 2004/0186359 A1 | 9/2004 | Beaudoin et al. |
| 2004/0199062 A1 | 10/2004 | Petersson et al. |
| 2004/0206916 A1 | 10/2004 | Colvin, Jr. et al. |
| 2004/0215134 A1 | 10/2004 | Soykan et al. |
| 2004/0249311 A1 | 12/2004 | Haar et al. |
| 2004/0254438 A1 | 12/2004 | Chuck et al. |
| 2004/0260162 A1 | 12/2004 | Rohleder et al. |
| 2005/0027176 A1 | 2/2005 | Xie |
| 2005/0033133 A1 | 2/2005 | Kraft |
| 2005/0038329 A1 | 2/2005 | Morris et al. |
| 2005/0042704 A1 | 2/2005 | Alarcon et al. |
| 2005/0043894 A1 | 2/2005 | Fernandez |
| 2005/0065464 A1 | 3/2005 | Talbot et al. |
| 2005/0065556 A1 | 3/2005 | Reghabi et al. |
| 2005/0070768 A1 | 3/2005 | Zhu et al. |
| 2005/0070770 A1 | 3/2005 | Dirac et al. |
| 2005/0070771 A1 | 3/2005 | Rule et al. |
| 2005/0096587 A1* | 5/2005 | Santini ................ A61B 5/4839 604/66 |
| 2005/0107677 A1* | 5/2005 | Ward ................ A61B 5/14532 600/347 |
| 2005/0113657 A1 | 5/2005 | Alarcon et al. |
| 2005/0113658 A1 | 5/2005 | Jacobson et al. |
| 2005/0130249 A1 | 6/2005 | Parris et al. |
| 2005/0137481 A1 | 6/2005 | Sheard et al. |
| 2005/0148832 A1 | 7/2005 | Reghabi et al. |
| 2005/0149139 A1 | 7/2005 | Plicchi et al. |
| 2005/0154272 A1 | 7/2005 | Dirac et al. |
| 2005/0221276 A1 | 10/2005 | Rozakis et al. |
| 2005/0221277 A1 | 10/2005 | Kawanishi |
| 2005/0228226 A1 | 10/2005 | Muckner |
| 2006/0025748 A1 | 2/2006 | Ye |
| 2006/0076236 A1 | 4/2006 | Shah et al. |
| 2006/0217771 A1 | 9/2006 | Soykan et al. |
| 2006/0229694 A1 | 10/2006 | Schulman et al. |
| 2006/0253043 A1 | 11/2006 | Zhang et al. |
| 2006/0270923 A1 | 11/2006 | Brauker et al. |
| 2007/0027495 A1 | 2/2007 | Gerber |
| 2007/0118056 A1 | 5/2007 | Wang et al. |
| 2007/0219628 A1 | 9/2007 | Shanley et al. |
| 2007/0252713 A1 | 11/2007 | Rondoni et al. |
| 2007/0270674 A1 | 11/2007 | Kane et al. |
| 2007/0270675 A1 | 11/2007 | Kane et al. |
| 2007/0275035 A1 | 11/2007 | Herman et al. |
| 2008/0033260 A1 | 2/2008 | Sheppard et al. |
| 2008/0046080 A1* | 2/2008 | Vanden Bulcke .. H01L 23/3107 623/10 |
| 2008/0077190 A1 | 3/2008 | Kane |
| 2008/0082001 A1 | 4/2008 | Hatlestad et al. |
| 2008/0152283 A1 | 6/2008 | Nielsen et al. |
| 2008/0294209 A1 | 11/2008 | Thompson et al. |
| 2009/0018425 A1 | 1/2009 | Ouyang et al. |
| 2009/0024045 A1 | 1/2009 | Prakash et al. |
| 2009/0076353 A1 | 3/2009 | Carpenter et al. |
| 2009/0124875 A1 | 5/2009 | Bentsen et al. |
| 2009/0221885 A1 | 9/2009 | Hall et al. |
| 2009/0312973 A1 | 12/2009 | Hatlestad et al. |
| 2010/0057057 A1* | 3/2010 | Hayter ................ A61B 5/4839 604/890.1 |
| 2010/0149544 A1 | 6/2010 | Ghislain |
| 2010/0280578 A1 | 11/2010 | Skelton et al. |
| 2010/0292634 A1 | 11/2010 | Bilmes et al. |
| 2011/0024307 A1 | 2/2011 | Simpson et al. |
| 2011/0098547 A1 | 4/2011 | Zhu et al. |
| 2011/0130666 A1 | 6/2011 | Dong et al. |
| 2013/0060105 A1* | 3/2013 | Shah ....................... A61B 5/742 600/316 |
| 2013/0150689 A1 | 6/2013 | Shaw-klein |
| 2013/0184599 A1 | 7/2013 | Friedman et al. |
| 2013/0197332 A1 | 8/2013 | Lucisano et al. |
| 2013/0338727 A1 | 12/2013 | Mokelke et al. |
| 2014/0018644 A1 | 1/2014 | Colvin et al. |
| 2014/0091945 A1* | 4/2014 | Rivas ................ A61B 5/7257 340/870.01 |
| 2014/0155710 A1 | 6/2014 | Rowland et al. |
| 2014/0187878 A1 | 7/2014 | Emken et al. |
| 2014/0276164 A1 | 9/2014 | Thakur et al. |
| 2014/0286875 A1 | 9/2014 | Gamsey et al. |
| 2014/0357964 A1 | 12/2014 | Wisniewski et al. |
| 2014/0364758 A1 | 12/2014 | Schindhelm et al. |
| 2015/0057509 A1 | 2/2015 | Huffstetler et al. |
| 2015/0164383 A1 | 6/2015 | Varsavsky et al. |
| 2015/0352229 A1 | 12/2015 | Brill et al. |
| 2016/0256063 A1 | 9/2016 | Friedman et al. |
| 2016/0363550 A1 | 12/2016 | Koo et al. |
| 2016/0374597 A1 | 12/2016 | Stahmann |
| 2017/0000359 A1* | 1/2017 | Kohli ..................... A61B 5/0022 |
| 2017/0215732 A1* | 8/2017 | Genier ................ A61B 5/0086 |
| 2017/0245788 A1* | 8/2017 | Heikenfeld .......... A61B 5/6832 |
| 2018/0055426 A1 | 3/2018 | Kane et al. |
| 2018/0153451 A1 | 6/2018 | Heikenfeld et al. |
| 2018/0263511 A1 | 9/2018 | Burnes et al. |
| 2018/0344218 A1 | 12/2018 | Li et al. |
| 2018/0350468 A1 | 12/2018 | Friedman et al. |

(56) References Cited

U.S. PATENT DOCUMENTS

| | | | |
|---|---|---|---|
| 2019/0029567 | A1 | 1/2019 | Stahmann et al. |
| 2019/0046032 | A1 | 2/2019 | Stahmann et al. |
| 2019/0125228 | A1 | 5/2019 | Kane et al. |
| 2019/0167112 | A1 | 6/2019 | Kane et al. |
| 2019/0167162 | A1 | 6/2019 | Li et al. |
| 2019/0336050 | A1 | 11/2019 | Deck et al. |
| 2022/0133177 | A1 | 5/2022 | Li et al. |
| 2022/0133178 | A1 | 5/2022 | Li et al. |
| 2022/0133234 | A1 | 5/2022 | Li et al. |

FOREIGN PATENT DOCUMENTS

| | | |
|---|---|---|
| JP | 2005287762 | 10/2005 |
| JP | 2005315871 | 11/2005 |
| JP | 2006507078 | 3/2006 |
| JP | 2006126715 | 5/2006 |
| JP | 2007525858 | 9/2007 |
| JP | 2009537247 | 10/2009 |
| WO | 9625978 | 8/1996 |
| WO | 9719188 | 5/1997 |
| WO | 9801071 | 1/1998 |
| WO | 9902651 | 1/1999 |
| WO | 0018289 | 4/2000 |
| WO | 0025862 | 5/2000 |
| WO | 0025863 | 5/2000 |
| WO | 0180728 | 11/2001 |
| WO | 2004039265 | 5/2004 |
| WO | 2004071291 | 8/2004 |
| WO | 2004081522 | 9/2004 |
| WO | 2004091719 | 10/2004 |
| WO | 2004092713 | 10/2004 |
| WO | 2005074612 | 8/2005 |
| WO | 2006017169 | 2/2006 |
| WO | 2007110867 | 10/2007 |
| WO | 2007137037 | 11/2007 |
| WO | 2008076491 | 6/2008 |
| WO | 2009038996 | 3/2009 |
| WO | 2013016573 | 1/2013 |
| WO | 2015048514 | 4/2015 |
| WO | 2016049019 | 3/2016 |
| WO | 2019023093 | 1/2019 |
| WO | 2019040635 | 2/2019 |

OTHER PUBLICATIONS

Final Office Action for U.S. Appl. No. 15/992,823 dated Aug. 13, 2020 (18 pages).
Final Office Action for U.S. Appl. No. 16/136,875 dated Aug. 21, 2020 (10 pages).
Non-Final Office Action for U.S. Appl. No. 16/041,923 dated Jul. 23, 2020 (61 pages).
Non-Final Office Action dated May 27, 2020 for U.S. Appl. No. 16/136,875, 43 pages.
Response to Communication Pursuant to Article 94(3) EPC for European Patent Application No. 18174561.3 filed Jul. 27, 2020 (11 pages).
Response to Non-Final Rejection dated Jun. 1, 2020 for U.S. Appl. No. 16/136,773, submitted via EFS-Web on Aug. 20, 2020, 10 pages.
Response to Non-Final Rejection dated Jun. 22, 2020 for U.S. Appl. No. 16/038,737, submitted via EFS-Web on Aug. 4, 2020, 10 pages.
Response to Non-Final Rejection dated May 27, 2020 for U.S. Appl. No. 16/136,875, submitted via EFS-Web on Jul. 22, 2020, 11 pages.
Response to Non-Final Rejection dated May 5, 2020 for U.S. Appl. No. 15/992,823, submitted via EFS-Web on Jul. 7, 2020, 10 pages.
Communication Pursuant to Article 94(3) EPC for European Patent Application No. 18174561.3 dated Jan. 27, 2020 (5 pages).
International Preliminary Report on Patentability for PCT Application No. PCT/US2018/043225 dated Feb. 6, 2020 (7 pages).
International Preliminary Report on Patentability for PCT Application No. PCT/US2018/047549 dated Mar. 5, 2020 (11 pages).
Response to Communication Pursuant to Rule 69 EPC for European Patent Application No. 18202201.2 filed Jan. 31, 2020 (22 pages).
Response to Communication Pursuant to Rule 69 EPC for European Patent Application No. 18209525.7 filed with the EPO Dec. 12, 2019 (33 pages).
Response to European Search Report for European Patent Application No. 18188253.1 filed Nov. 7, 2019 (14 pages).
Response to Extended European Search Report for European Patent Application No. 18207668.7 filed Nov. 29, 2019 (14 pages).
Extended European Search Report for European Patent Application No. 18202201.2 dated Jun. 28, 2019 (9 pages).
Response to Communication Pursuant to Rule 69 EPC for European Patent Application No. 18174561.3 filed Jun. 3, 2019 (21 pages).
Anderson, J. M. et al., "Monocyte, Macrophage and foreign body giant cell interactions with molecularly engineered surfaces," Journal of Materials Science: Materials in Medicine 10 (1999) 579-588 (10 pages).
Anderson, James M. "Biological Responses to Materials," Annu. Rev. Mater. Res. 2001. 31:81-110 (30 pages).
Anderson, James M. et al., "Foreign Body Reaction to Biomaterials," Semin. Immunol. Apr. 2008; 20(2): 86-100 (27 pages).
Bakker, Eric et al., "Carrier-Based Ion-Selective Electrodes and Bulk Optodes. 1. General Characteristics," Chem. Rev. 1997, 97, 3083-3132 (50 pages).
Benco, John S. et al., "Optical Sensors for Blood Analytes," The Spectrum, vol. 14, Issue 4, pp. 4-11, Winter 2001 (8 pages).
Bender, J. W. et al., "The Use of Biomedical Sensors to Monitor Capsule Formation Around Soft Tissue Implants," Annals of Plastic Surgery, vol. 56, No. 1, Jan. 2006, pp. 72-77 (6 pages).
Bridges, Amanda W. et al., "Anti-Inflammatory Polymeric Coatings for Implantable Biomaterials and Devices," Journal of Diabetes Science and Technology 2008;2(6):984-994 (11 pages).
Buhlmann, Philippe et al., "Carrier-Based Ion-Selective Electrodes and Bulk Optodes. 2. Ionophores for Potentiometric and Optical Sensors," Chem. Rev. 1998, 98, 1593-1687 (95 pages).
"Communication Pursuant to Article 94(3) EPC," for European Patent Application No. 07762189.4 dated Mar. 24, 2009 (3 pages).
"Communication pursuant to Article 94(3) EPC," for European Patent Application No. 07762189.4 dated Mar. 16, 2010 (3 pages).
"Extended European Search Report," for European Patent Application No. 18174561.3 dated Aug. 28, 2018 (9 pages).
File History for U.S. Appl. No. 11/383,926.
File History for U.S. Appl. No. 11/383,933.
File History for U.S. Appl. No. 11/856,850.
File History for U.S. Appl. No. 12/391,761.
"First Examination Report," for Australian Patent Application No. 2008302499 dated Feb. 8, 2011 (1 page).
Han, In S. et al., "Constant-Volume Hydrogel Osmometer: A New Device Concept for Miniature Biosensors," Biomacromolecules, Mar. 2002, pp. 1271-1275 (5 pages).
He, Huarui et al., "Enantioselective Optodes," Analytica Chimica Acta, 246, pp. 251-257, 1991 (7 pages).
He, Wei et al., "A Novel Anti-inflammatory Surface for Neural Electrodes," Adv. Mater. 2007, 19, 3529-3533 (5 pages).
Helton, Kristen L. et al., "Biomechanics of the Sensor-Tissue Interface-Effects of Motion, Pressure, and Design on Sensor Performance and the Foreign Body Response—Part I: Theoretical Framework," Journal of Diabetes Science and Technology 2011;5(3):632-646 (15 pages).
"International Preliminary Report on Patentability," for PCT Application No. PCT/US2008/075673 dated Mar. 24, 2010 (6 pages).
"International Search Report and Written Opinion," for PCT Application No. PCT/US2008/075673 dated Nov. 28, 2008 (13 pages).
Koh, Ahyeon et al., "Glucose Sensor Membranes for Mitigating the Foreign Body Response," Journal of Diabetes Science and Technology 2011;5(5):1052-1059 (8 pages).
Koronczi, et al., "Development of a submicron optochemical potassium sensor with enhanced stability due to internal reference," Sensors and Actuators B, 51:188-195 (1998).
Kuwana, Eddy et al., "Sensing of pH in Multiply Scattering Media with Fluorescence Lifetime," Advanced Biomedical and Clinical Diagnostic Systems, Proceedings of SPIE, vol. 4958, pp. 32-42, 2003 (11 pages).

(56) References Cited

OTHER PUBLICATIONS

Lehn, J. M. et al., "[2]-Cryptates: Stability and Selectivity of Alkali and Akaline-Earth Macrobicycle Complexes," Journal of the American Chemical Society, Nov. 12, 1975 pp. 6700-6707 (8 pages).
Lima-Oliveira, Gabriel et al., "Patient Posture for Blood Collection by Venipuncture: Recall for Standardization After 28 Years," Brazilian Journal of Hematology and Hemotherapy 2017 <http://dx.doi.org/10.1016/j.bjhh.2017.01.004> (6 pages).
Messler, "The Joining of Materials," Nov. 2004 (58 pages).
"Microminiature Device Monitors Vital Electrolytes and Metabolites," John Glenn Biomedical Engineering Consortium, May 2002 (2 pages).
"Microminiature Monitor for Vital Electrolyte and Metabolite Levels of Astronauts—Status Report," John Glenn Biomedical Engineering Consortium NASA Glenn Research Center at Lewis Field, Apr. 2003 (5 pages). NASA Glenn Research Center at Lewis Field.
Novak, Matthew T. et al., "Modeling the relative impact of capsular tissue effects on implanted glucose sensor time lag and signal attenuation," Anal. Bioanal. Chem. Oct. 2010; 398(4):1695-1705 (22 pages).
"Office Action," for Japanese Patent Application No. 2010-524940 dated Nov. 22, 2011 (8 pages) with English translation.
Padmanabhan, Jagnnath et al., "Nanomaterials, Inflammation and Tissue Engineering," Wiley Interdiscip Rev Nanomed Nanobiotechnol. May 2015;7(3):355-370 (23 pages).
"PCT International Search Report and Written Opinion," for International Application No. PCT/US2007/068954, dated Nov. 17, 2008 (12 pages).
"Response to Communication Pursuant to Article 94(3) EPC," for European Patent Application No. 07762189.4 filed with the EPO dated Jul. 27, 2009 (9 pages).
Roger, Yvonne et al., "Grid-like surface structures in thermoplastic polyurethane induce anti-inflammatory and anti-fibrotic processes in bone marrow-derived mesenchymal stem cells," Abstract Only Colloids and Surfaces B: Biointerfaces vol. 148, Dec. 2016, pp. 104-115 (4 pages).
Seelig, Mildred S. "Electrographic Patterns of Magnesium Depletion Appearing in Alcoholic Heart Disease," Annals of the New York Academy of Sciences, vol. 162, Article 2, 1969, pp. 906-917 (13 pages).
Sharkawy, A. A. et al., "Engineering the tissue which encapsulates subcutaneous implants. I. Diffusion properties," Department of Biomedical Engineering, NSF Center for Emerging Cardiovascular Technology, Duke University, Durham, North Carolina 1996 (12 pages).
Shirreffs, S. M. "The Effect of Posture Change on Blood Volume Serum Potassium, and Whole Body Electrical Impedance," Eur. J. Appl. Physiol. (1994)69:461-463 (3 pages).
Tohda, Koji et al., "A Microscopic, Continuous, Optical Monitor for Interstitial Electrolytes and Glucose," Chemphyschem 2003, pp. 155-160 (6 pages).
Tohda, Koji et al., "Micro-miniature Autonomous Optical Sensor Array for Monitoring Ions and Metabolites 1: Design, Fabrication, and Data Analysis," Analytical Sciences, Mar. 2006, vol. 22 pp. 383-388 (6 pages).
Tsai, Hc et al., "Simultaneous Determination of Renal Clinical Analytes in Serum using Hydrolase- and Oxidase-Encapsulated Optical Array Biosensors," Analytical Biochemistry 334 (2004) 183-192 (10 pages).
"Upconverting nanoparticles," Wikipeda.com accessed Jun. 12, 2017 (13 pages).
Voskericican, Gabriela et al., "Biocompatibility and Biofouling of MEMs Drug Delivery Devices," Biomaterials 24 (2003) 1959-1967 (9 pages).
Weisberg, Lawrence S. "Management of Severe Hyperkalemia," Crit Care Med 2008 vol. 36, No. 12 (6 pages).
"Extended European Search Report," for European Patent Application No. 18209525.7 dated Feb. 27, 2019 (12 pages).
"International Search Report and Written Opinion," for PCT Application No. PCT/US2018/043225 dated Nov. 16, 2018 (11 pages).
"Partial European Search Report," for European Patent Application No. 18188253.1 dated Jan. 7, 2019 (11 pages).
International Search Report and Written Opinion for PCT Application No. PCT/US2018/047549 dated Oct. 26, 2018 (15 pages).
Extended European Search Report for European Patent Application No. 18188253.1 dated Apr. 9, 2019 (10 pages).
Extended European Search Report for European Patent Application No. 18207668.7 dated Apr. 3, 2019 (7 pages).
Non-Final Office Action for U.S. Appl. No. 15/992,823 dated May 5, 2020 (51 pages).
Non-Final Office Action for U.S. Appl. No. 16/038,737 dated Jun. 22, 2020 (46 pages).
Non-Final Office Action for U.S. Appl. No. 16/136,773 dated Jun. 1, 2020 (43 pages).
Non-Final Office Action for U.S. Appl. No. 16/136,875 dated May 27, 2020 (43 pages).
Communication Pursuant to Article 94(3) EPC for European Patent Application No. 18207668.7 dated Jan. 13, 2021 (4 pages).
Non-Final Office Action for U.S. Appl. No. 16/041,923 dated Feb. 2, 2021 (39 pages).
Non-Final Office Action for U.S. Appl. No. 16/136,875 dated Jan. 25, 2021 (12 pages).
Response to Final Rejection dated Nov. 2, 2020 for U.S. Appl. No. 16/038,737, submitted via EFS-Web on Feb. 2, 2021, 9 pages.
Communication Pursuant to Article 94(3) EPC for European Patent Application No. 18209525.7 dated Dec. 8, 2020 (5 pages).
Final Office Action for U.S. Appl. No. 16/038,737 dated Nov. 2, 2020 (15 pages).
Non-Final Office Action for U.S. Appl. No. 15/992,823 dated Dec. 23, 2020 (18 pages).
Notice of Allowance for U.S. Appl. No. 16/136,773 dated Nov. 18, 2020 (17 pages).
Response to Communication Pursuant to Article 94(3) EPC for European Patent Application No. 18207668.7 filed Dec. 11, 2020 (65 pages).
Response to Communication Pursuant to Rules 161(1) and 162 EPC for European Patent Application No. 18773017.1 filed Sep. 30, 2020 (13 pages).
Response to Final Rejection dated Aug. 13, 2020 for U.S. Appl. No. 15/992,823, submitted via EFS-Web on Oct. 13, 2020, 9 pages.
Response to Final Rejection dated Aug. 21, 2020 and Advisory Action dated Oct. 19, 2020 for U.S. Appl. No. 16/136,875, submitted via EFS-Web on Nov. 20, 2020, 14 pages.
Response to Final Rejection dated Aug. 21, 2020 for U.S. Appl. No. 16/136,875, submitted via EFS-Web on Oct. 13, 2020, 12 pages.
Response to Non-Final Rejection dated Jul. 23, 2020 for U.S. Appl. No. 16/041,923, submitted via EFS-Web on Oct. 13, 2020, 12 pages.
"Non-Final Office Action," for U.S. Appl. No. 16/038,737 dated Mar. 24, 2021 (14 pages).
"Response to Non-Final Rejection," dated Dec. 23, 2020 for U.S. Appl. No. 15/992,823, submitted via EFS-Web on Mar. 23, 2021, 9 pages.
"Response to Non-Final Rejection," dated Feb. 2, 2021 for U.S. Appl. No. 16/041,923, submitted via EFS-Web on Mar. 17, 2021, 12 pages.
"Response to Non-Final Rejection," dated Jan. 25, 2021 for U.S. Appl. No. 16/136,875, submitted via EFS-Web on Mar. 17, 2021, 12 pages.
"Final Office Action," for U.S. Appl. No. 16/041,923 dated Jul. 9, 2021 (29 pages).
"Notice of Allowance," for U.S. Appl. No. 15/992,823 dated Jun. 10, 2021 (16 pages).
"Response to Communication Pursuant to Article 94(3) EPC," for European Patent Application No. 18207668.7 filed May 21, 2021 (32 pages).
"Response to Communication Pursuant to Article 94(3) EPC," for European Patent Application No. 18209525.7 filed Apr. 15, 2021 (10 pages).
"Response to Non-Final Rejection," dated Mar. 24, 2021 for U.S. Appl. No. 16/038,737, submitted via EFS-Web on Jun. 18, 2021, 11 pages.
"Final Office Action," for U.S. Appl. No. 16/038,737 dated Sep. 7, 2021 (12 pages).

(56) References Cited

OTHER PUBLICATIONS

"Non-Final Office Action," for U.S. Appl. No. 16/130,638 dated Aug. 23, 2021 (67 pages).
"Response to Final Rejection," mailed on Jul. 9, 2021 and Advisory Action dated Sep. 20, 2021 for U.S. Appl. No. 16/041,923, submitted via EFS-Web on Sep. 27, 2021, 12 pages.
"Response to Final Rejection," dated Jul. 9, 2021 for U.S. Appl. No. 16/041,923, submitted via EFS-Web on Sep. 9, 2021, 12 pages.
"First Office Action," for Chinese Patent Application No. 201710730979.1 dated Apr. 11, 2022 (23 pages) with English Translation.
"International Search Report and Written Opinion," for PCT Application No. PCT/US2021/056590 dated May 3, 2022 (14 pages).
"Non-Final Office Action," for U.S. Appl. No. 16/041,923 dated May 23, 2022 (22 pages).
"Non-Final Office Action," for U.S. Appl. No. 16/130,638 dated May 6, 2022 (13 pages).
"Notice of Allowance," for U.S. Appl. No. 16/038,737 dated May 18, 2022 (13 pages).
"Response to Non-Final Rejection," dated Mar. 3, 2022 for U.S. Appl. No. 16/038,737, submitted via EFS-Web on May 4, 2022, 10 pages.
"Final Office Action," for U.S. Appl. No. 16/130,638 dated Jan. 26, 2022 (16 pages).
"First Office Action," for Chinese Patent Application No. 201710400287.0 dated Dec. 23, 2021 (37 pages) with English Translation.
"First Office Action," for Chinese Patent Application No. 201710681567.3 dated Mar. 18, 2022 (16 pages) with English Translation.
"International Search Report and Written Opinion," for PCT Application No. PCT/US2021/056602 dated Feb. 9, 2022 (12 pages).
"Invitation to Pay Additional Fees," for PCT Application No. PCT/US2021/056590 dated Mar. 9, 2022 (9 pages).
"Non-Final Office Action," for U.S. Appl. No. 16/038,737 dated Mar. 3, 2022 (17 pages).
"Non-Final Office Action," for U.S. Appl. No. 16/041,923 dated Nov. 15, 2021 (21 pages).
"Response to Final Rejection," dated Jan. 26, 2022 and the Advisory Action dated Apr. 18, 2022 for U.S. Appl. No. 16/130,638, submitted via EFS-Web on Apr. 26, 2022, 7 pages.
"Response to Final Rejection," dated Jan. 26, 2022 for U.S. Appl. No. 16/130,638, submitted via EFS-Web on Mar. 24, 2022, 8 pages.
"Response to Final Rejection," dated Sep. 7, 2021 for U.S. Appl. No. 16/038,737, submitted via EFS-Web on Nov. 30, 2021, 10 pages.
"Response to Non-Final Rejection," dated Aug. 23, 2021 for U.S. Appl. No. 16/130,638, submitted via EFS-Web on Nov. 1, 2021, 9 pages.
"Response to Non-Final Rejection," dated Nov. 15, 2021 for U.S. Appl. No. 16/041,923, submitted via EFS-Web on Feb. 9, 2022, 7 pages.
"Response to Non-Final Rejection," dated May 23, 2022 for U.S. Appl. No. 16/041,923, submitted via EFS-Web on Aug. 23, 2022, 11 pages.
"Response to Non-Final Rejection," dated May 6, 2022 for U.S. Appl. No. 16/130,638, submitted via EFS-Web on Aug. 5, 2022, 7 pages.

* cited by examiner

IMPLANTABLE CHEMICAL SENSOR WITH STAGED ACTIVATION

This application claims the benefit of China Patent Application No. 201710730979.1, filed Aug. 23, 2017, the content of which is herein incorporated by reference in its entirety.

FIELD

Embodiments herein include implantable medical devices including chemical sensors with bioerodible masking layers to allow for staged activation of the sensors.

BACKGROUND

Data regarding physiological analytes are highly relevant for the diagnosis and treatment of many conditions and disease states. As one example, potassium ion concentrations can affect a patient's cardiac rhythm. Therefore, medical professionals frequently evaluate physiological potassium ion concentration when diagnosing a cardiac rhythm problem. However, measuring physiological concentrations of analytes, such as potassium, generally requires drawing blood from the patient. Blood draws are commonly done at a medical clinic or hospital and therefore generally require the patient to physically visit a medical facility. As a result, despite their significance, physiological analyte concentrations are frequently measured only sporadically.

Implantable chemical sensors can be used to gather data about physiological analytes while a patient is away from a medical care facility and without needing to draw blood or another fluid from the patient. However, many implantable chemical sensors have a limited useful life span due to intrinsic design limitations, biofouling, the host's foreign body response, and the like.

SUMMARY

Embodiments herein include implantable medical devices including chemical sensors with bioerodible masking layers to allow for staged activation of the sensors.

In a first aspect, an implantable medical device is included. The implantable medical device can include a substrate defining wells and a first chemical sensor and a second chemical sensor disposed within separate wells of the substrate. The first chemical sensor and the second chemical sensor can be configured to detect one or more analytes. A first bioerodible masking layer can be disposed over the second chemical sensor and can seal off the second chemical sensor. The first bioerodible masking layer can include a first material having a first erosion rate and a protective planarization layer disposed over at least one of the first chemical sensor and the second chemical sensor such that the outermost surface of the medical device over the first sensor is flush with the outermost surface of the medical device over the second sensor. The planarization layer can include a second material having an erosion rate that is faster than the erosion rate of the first bioerodible masking layer.

In a second aspect, in addition to or in place of other aspects herein, each of the first chemical sensor and second chemical sensor can include a sensing element and an analyte window disposed on the top of the sensing element.

In a third aspect, in addition to or in place of other aspects herein, the first sensor becomes exposed to an in vivo environment after erosion of the protective planarization layer, but the second sensor remains isolated from the in vivo environment because of the first bioerodible masking layer.

In a fourth aspect, in addition to or in place of other aspects herein, the first chemical sensor is configured to be active more quickly after implantation of the implantable medical device into a patient than the second chemical sensor.

In a fifth aspect, in addition to or in place of other aspects herein, the device further includes a solution having a greater than physiologic concentration of one or more analytes that the second chemical sensor is configured to detect and the solution permeates the second chemical sensor and is sealed in by the first bioerodible masking layer.

In a sixth aspect, in addition to or in place of other aspects herein, the device further includes a solution containing an optical dye, wherein the solution permeates the second chemical sensor and is sealed in by the first bioerodible masking layer.

In a seventh aspect, in addition to or in place of other aspects herein, the device further includes a third chemical sensor, wherein a second bioerodible masking layer is disposed over the third chemical sensor, the second bioerodible masking layer comprising a third material having an erosion rate that is different that the erosion rate of the first bioerodible masking layer.

In an eighth aspect, in addition to or in place of other aspects herein, the erosion rate of the first bioerodible masking layer is faster than erosion rate of the second bioerodible masking layer.

In a ninth aspect, in addition to or in place of other aspects herein, the device further includes a third chemical sensor, wherein a second bioerodible masking layer is disposed over the third chemical sensor, wherein the second bioerodible masking layer is thicker than the first bioerodible masking layer.

In a tenth aspect, in addition to or in place of other aspects herein, the first and second bioerodible masking layers can include one or more of polylactic acid (PLA), poly-L-lactic acid (PLLA), poly-lactide-co-glycolide (PLGA), poly-D, L-lactide-(PDLA), polyglycolide, polyhydroxyalkanoate, polyhydroxybuterate, or polycarbonate.

In an eleventh aspect, in addition to or in place of other aspects herein, the analyte window can be formed from a hydrophilic polymer.

In a twelfth aspect, in addition to or in place of other aspects herein, the analyte window can be formed from polyhydroxyethyl methacrylate (polyHEMA).

In a thirteenth aspect, in addition to or in place of other aspects herein, the planarization layer can be formed from a material selected from the group consisting of an agglomerated material, a sugar, hydroxypropyl ethyl cellulose and hydroxypropyl methylcellulose.

In a fourteenth aspect, an implantable medical device is included. The device can have a substrate defining wells and a first chemical sensor and a second chemical sensor disposed within separate wells of the substrate. The first chemical sensor and the second chemical sensor can be configured to detect one or more analytes. Each of the first chemical sensor and second chemical sensor can include a sensing element. The device can further include a first bioerodible masking layer disposed over the second chemical sensor that can seal off the second chemical sensor. The first bioerodible masking layer can include a first material having a first erosion rate and a protective planarization layer disposed over at least one of the first chemical sensor and the second chemical sensor such that the outermost surface of the medical device over the first sensor is flush with the outermost surface of the medical device over the second sensor. The planarization layer can include a second material having an erosion rate that is faster than the erosion rate of the first bioerodible masking layer. The device can further include a detector unit comprising a processor, the detector unit can be configured to monitor an operational status of at least the first chemical sensor and second chemical sensor.

In a fifteenth aspect, in addition to or in place of other aspects herein, the first chemical sensor can be configured to be in an active status immediately after implantation and the second chemical sensor can be configured to be in an inactive status immediately after implantation.

In a sixteenth aspect, in addition to or in place of other aspects herein, the detector unit can be configured to compare the operational status of the first chemical sensor to the operational status of the second chemical sensor.

In a seventeenth aspect, in addition to or in place of other aspects herein, the detector unit can be configured to periodically evaluate the second chemical sensor status to monitor the sensed concentration of the analyte in order to assess the erosion status of the first bioerodible masking layer.

In a eighteenth aspect, in addition to or in place of other aspects herein, the detector unit can be configured to calculate the response time of the first sensor and the response time of the second sensor and compare the two response times.

In a nineteenth aspect, in addition to or in place of other aspects herein, the detector can determine that the second sensor is ready for active use when the concentration of the analyte sensed by the second chemical sensor status falls to physiological levels and the response time of the second sensor is within 5% of the response time of the second sensor.

In a twentieth aspect, in addition to or in place of other aspects herein, the detector unit can be configured to disable the first chemical sensor when it is determined that the second chemical sensor is ready for active use and the determination that the second chemical sensor is ready for active use can be made by the implantable medical device or is received by the implantable medical device from an external source This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

Implantable chemical sensors can be used to gather data about physiological analytes while a patient is away from a medical care facility and without needing to draw blood or another fluid from the patient. However, many implantable chemical sensors have a limited useful life span due to intrinsic design limitations, biofouling, the host's foreign body response, and the like.

In various embodiments herein, implantable medical devices are equipped with multiple chemical sensors, some of which are initially sealed off from exposure to the in vivo environment after implantation, but later exposed after erosion of a masking layer. In this way, the ability to sense analytes is extended beyond the useful life of just a single sensor because some are only exposed to the in vivo environment and activated later.

Figure 1:
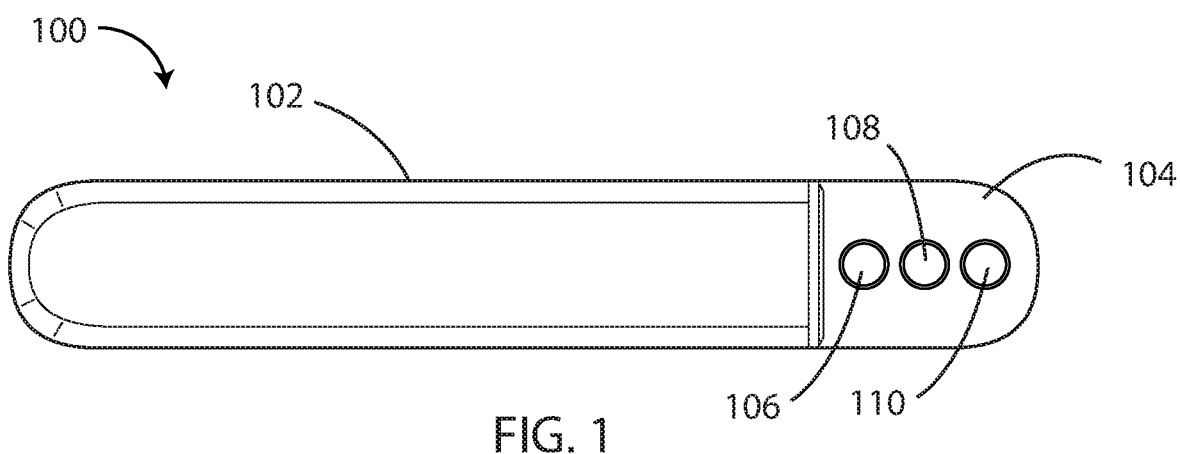
FIG. 1 is a schematic top view of an implantable medical device in accordance with the embodiments herein.

Referring now to FIG. 1, an implantable medical device (IMD) 100 is shown in accordance with the embodiments herein. The IMD 100 can include an implantable housing 102 and a header 104 coupled to the implantable housing 102. Various materials can be used. However, in some embodiments, the housing 102 can be formed of a material such as a metal, ceramic, a polymer, or a composite. The header 104 can be formed of various materials, but in some embodiments the header 104 can be formed of a translucent polymer such as an epoxy material. In some embodiments the header 104 can be hollow. In other embodiments the header 104 can be filled with components and/or structural materials such as epoxy or another material such that it is non-hollow.

The IMD 100 can also include an array of chemical sensors 106, 108, and 110 coupled to the implantable housing 102. Chemical sensors 106, 108, and 110 can each be configured to detect an analyte, such as an ion concentration of a bodily fluid, when implanted in the body. Bodily fluids can include blood, interstitial fluid, serum, lymph, serous fluid, cerebrospinal fluid, and the like. In some embodiments, chemical sensors 106, 108, and 110 can be configured to detect one or more of an electrolyte, a protein, a sugar, a hormone, a peptide, an amino acid, a metabolic product or the like. In some embodiments, the chemical sensors 106, 108, and 110 can be configured to detect an ion selected from the group consisting of potassium, sodium, chloride, calcium, magnesium, lithium, hydronium, hydrogen phosphate, bicarbonate, and the like. In some embodiments, the sensors 106, 108, and 110 can be configured to detect creatinine or glucose. However, many other physiological analytes are also contemplated herein and are discussed further below.

It will be appreciated that the array of chemical sensors 106, 108, and 110 can be positioned at any location along IMD 100, including along the implantable housing 102 and along the header 104. It will also be appreciated that though FIG. 1 shows an array having only three chemical sensors 106, 108, and 110, any number of chemical sensors can be present in the array. For example, the array may include at least 1, 2, 3, 4, 5, 6, 7, 8, 9, 10, 11, 12, or more chemical sensors. In some embodiments the chemical sensors 106, 108, and 110 can be configured to detect the same analyte, whereas in other embodiments, the chemical sensors 106, 108, and 110 can be configured to detect different analytes.

The IMB 100 can take on various dimensions. In a particular embodiment herein, the IMB 100 can be approximately 2 to 3 inches in length, 0.4 to 0.6 inches wide, and 0.15 to 0.35 inches thick. However, in some embodiments, the IMB 100 can be about 0.25, 0.5, 1.0, 2.0, 3.0, 4.0, or 5.0 inches in length. In some embodiments the length can be in a range wherein any of the foregoing lengths can serve as the upper or lower bound of the range, provided that the upper bound is greater than the lower bound. In some embodiments, the IMB 100 can be about 0.25, 0.5, 0.75, 1.0, or 2.0 inches in width. In some embodiments the length can be in a range wherein any of the foregoing widths can serve as the upper or lower bound of the range, provided that the upper bound is greater than the lower bound. In some embodiments, the IMB 100 can be about 0.10, 0.25, 0.50, 0.75 or 1.0 inches thick. In some embodiments the thickness can be in a range wherein any of the foregoing thicknesses can serve as the upper or lower bound of the range, provided that the upper bound is greater than the lower bound.

Figure 2:
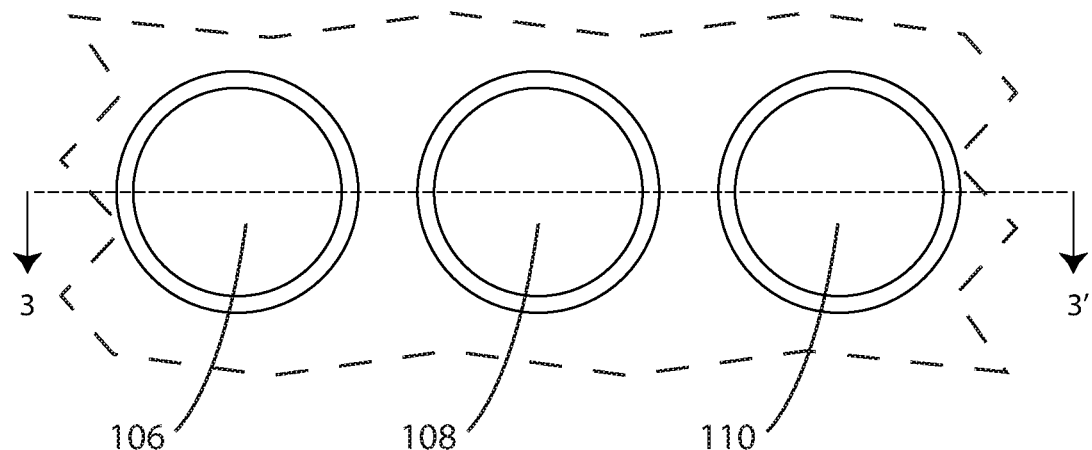
FIG. 2 is a schematic view of an array of chemical sensors in accordance with various embodiments herein.

Referring now to FIG. 2, a top-down view of the array of chemical sensors 106, 108, and 110 is shown magnified with respect to FIG. 1. Chemical sensors 106, 108, and 110 are shown as circles, however, it will be appreciated that the chemical sensors embodied herein can take on many geometric shapes and sizes, including but not limited to squares, ovals, triangles, rectangles, pentagons, octagons, parallelograms, etc.

Figure 3:
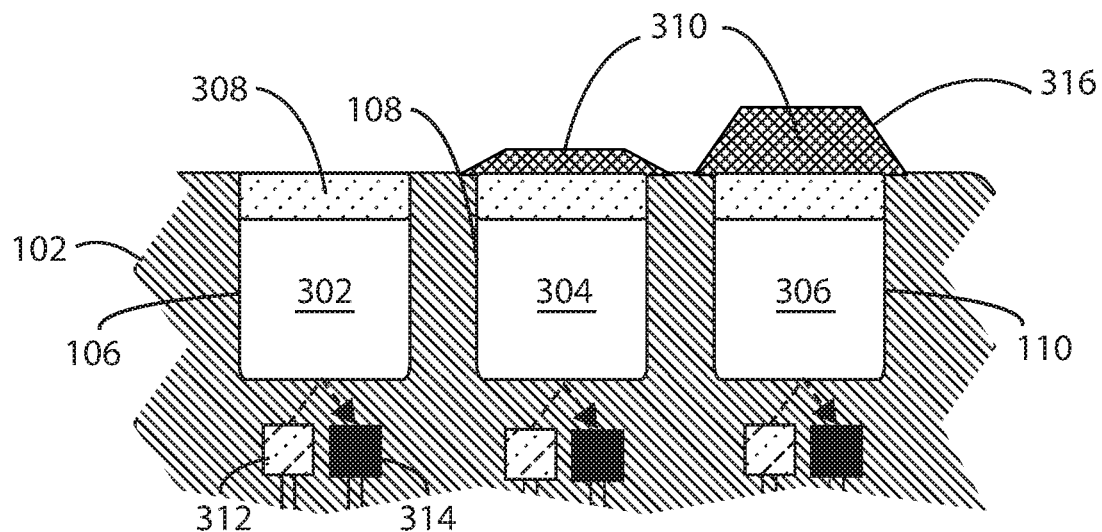
FIG. 3 is a cross-sectional view of an array of chemical sensors taken along line 3-3' of FIG. 2.

Referring now to FIG. 3, a cross-sectional view of chemical sensors 106, 108, and 110 along line 3-3' of FIG. 2 is shown. Chemical sensors 106, 108, and 110 can include, but not be limited to, sensing elements 302, 304, and 306, respectively. Each of the chemical sensors 106, 108, and 110 can also include an analyte window 308 disposed on the top of sensing elements 302, 304, and 306.

Each analyte window 308 can be formed from a permeable material, such as an ion permeable polymeric matrix material. Many different materials can be used as the ion permeable polymeric matrix material. In some embodiments, the ion permeable polymeric matrix material can be a hydrogel. In some embodiments, the ion permeable polymeric matrix material can be polyhydroxyethyl methacrylate (polyHEMA) either as a homopolymer or a copolymer including the same. The ion permeable polymeric matrix material(s) can be chosen based on its permeability to one or more of an electrolyte, a protein, a sugar, a hormone, a peptide, an amino acid, or a metabolic product. Specific ion permeable polymeric matrix material are discussed in more detail below.

FIG. 3 shows chemical sensors 106, 108, and 110 as optical chemical sensors. However, in other embodiments the chemical sensors can be an electrochemical sensor such as a potentiometric or voltammetric sensor, electrical sensor, etc., as discussed in more detail below. The optical chemical sensors can include optical excitation 312 and optical detection 314 assemblies. Suitable optical excitation and optical detection assemblies for use herein are discussed in more detail below.

In accordance with the embodiments herein, some of the chemical sensors can also include a bioerodible masking layer disposed on or over the exterior surface of the chemical sensor or the analyte window (if one is included) so as to shield the chemical sensors from the implant environment until a predetermined point in time. Masking layer 310 can be formed from various bioerodible polymers including, but not limited to, polylactic acid, poly-L-lactic acid, and derivatives thereof. Additional masking layer materials and their physical properties suitable for use with the embodiments herein are described more fully below.

In some embodiments, each masking layer 310 can be designed such that the chemical sensor remains isolated, and therefore largely inactive, until degradation of the masking layer materials. The size and composition of each masking layer 310 can be configured to decompose and activate the underlying chemical sensor at a specific point in time. In some embodiments, the size and composition of each masking layer 310 can be the same. In some embodiments, the size and composition of each masking layer 310 can be different. Specific details regarding sensor activation and deactivation are described more fully below.

In some embodiments, each masking layer 310 can be any of the following thicknesses: 50 µm, 75 µm, 100 µm, 200 µm, 250 µm, 300 µm, 400 µm, 500 µm, 1 mm, or 2 mm thick. In some embodiments the thickness of each masking layer can independently be in a range wherein any of the foregoing thicknesses can serve as the upper or lower bound of the range, provided that the upper bound is greater than the lower bound. In some embodiments, the masking layer 310 can be between 50-250 µm. In some embodiments, the masking layer 310 can be between 0.25-1.0 mm thick. In some embodiments, each masking layer 310 disposed on the exterior surface of the analyte window(s) 308 can be a different thickness. In some embodiments, the masking layer 310 disposed on the exterior surface of the analyte window(s) 308 can be the same thickness, but made of different materials.

In some embodiments, masking layer 310 can include a tapered edge 316 on its outer perimeter. This tapered edge 316 can provide protection to the masking layer 310 from accidental removal by frictional forces during implantation. The tapered edge 316 can be on all sides of the masking layer 310 or only on certain sides. In some embodiments, the tapered edge can have a slope of about 10 degrees to about 80 degrees. However, it will also be appreciated that the masking layer 310 can also be configured such that it does not include a tapered edge 316 in some embodiments.

Figure 4:
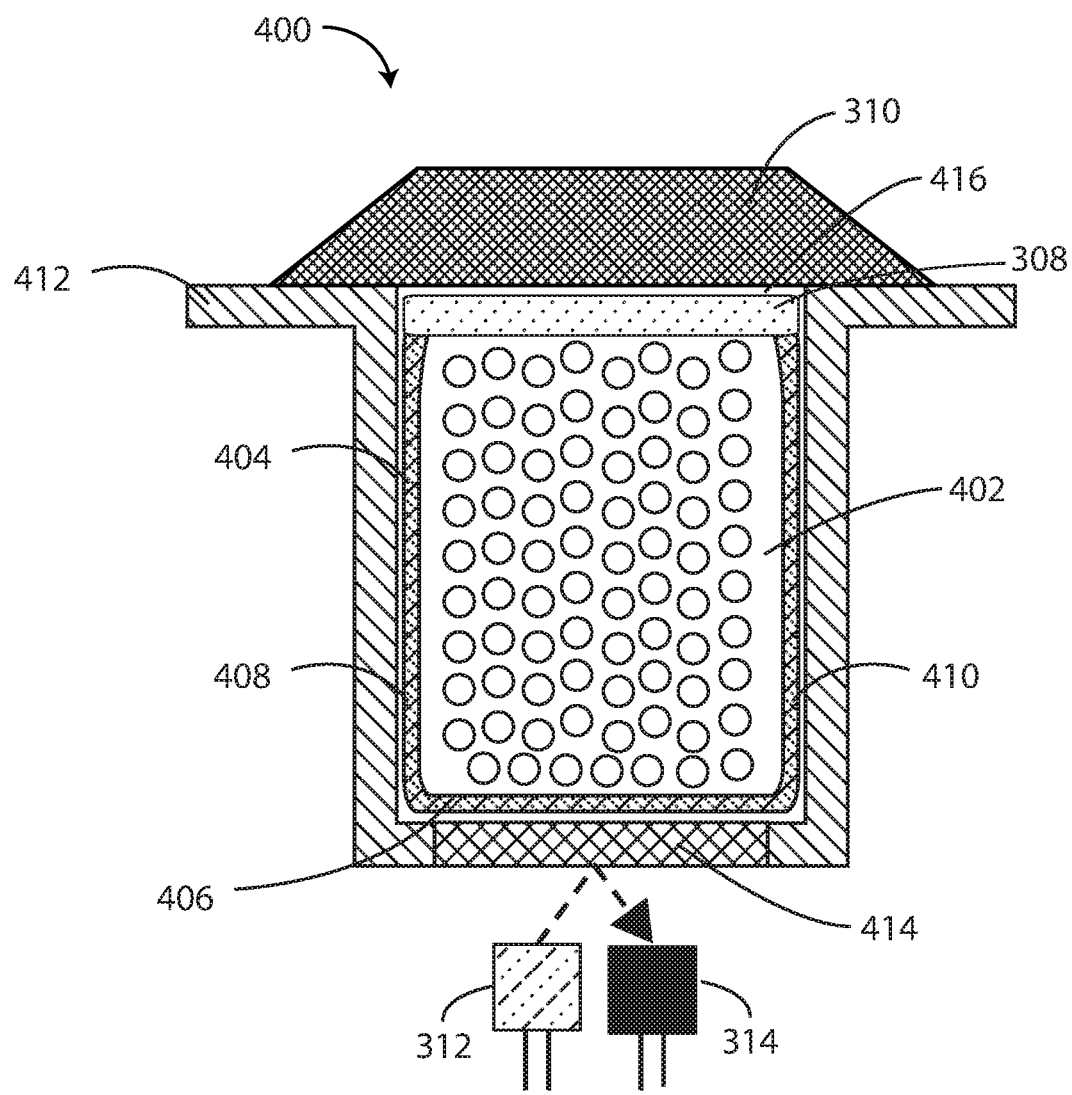
FIG. 4 is a cross-sectional view of a chemical sensor in accordance with the embodiments herein.

Referring now to FIG. 4, a cross-sectional view of a chemical sensor 400 in accordance with the embodiments herein is shown. Chemical sensor 400 can include sensing element 402, analyte window 308, and masking layer 310. The sensing element 402 can include an outer barrier layer 404 formed, in full or in part, from a permeable material, such as the ion permeable polymeric matrix materials as described below. Outer barrier layer 404 can include a bottom 406, and opposed sides 408 and 410 to surround an interior volume of sensing element 402. In some embodiments, analyte window 308 can be integrated with and/or form the top of the outer barrier layer 404 and in some cases be the same material as the other portions of the outer barrier layer 404. In other embodiments, analyte window 308 can be formed from a different material than the outer barrier layer 404. In some embodiments, only the analyte window 308 can be permeable to an analyte. In some embodiments, the entire outer barrier layer 404 can be permeable to an analyte. In some embodiments, the analyte window can be created from the ion permeable polymeric matrix material, polyhydroxyethyl methacrylate (polyHEMA).

In some embodiments, the implantable housing 102 can include a recessed pan 412 into which the sensing element 402 fits. In some embodiments, the top of the recessed pan 412 can be substantially flush with the top of the sensing element 402. In other embodiments, the top of the recessed pan 412 can be higher than the top of the sensing element 402 so as to create a space 416 between the top of the sensing element 402 and the top of the recessed pan. In some embodiments, the space 416 can be covered by masking layer 310. In some embodiments, the space 416 can be filled with a solution, which can also permeate the sensing element, having a concentration of an analyte that is greater than or less than that of a physiological concentration of the same analyte. As just one example, assuming the sensing element is specific for sensing potassium ion, the space 416 can be filled with, and the sensing element can be permeated by, a solution having a concentrate of potassium ions that is greater than possible physiological value, such as a 7 mM potassium ion solution.

In some embodiments, implantable housing 102 can define an aperture occluded by a transparent member 414. The transparent member 414 can be a glass (including but not limited to borosilicate glasses), a polymer or other transparent material. The aperture can be disposed at the bottom of the recessed pan 412. The aperture can provide an interface allowing for optical communication between sensing element 402 and the optical excitation 312 and optical detection 314 assemblies.

It will be appreciated that outer barrier layer 404, or portions thereof such as the bottom 406, can be made from a transparent polymer matrix material to allow for optical communication between the sensing element 402 and optical excitation 312 and optical detection 314 assemblies. In will be appreciated, however, that bottom 406 of sensing element 402 may or may not be a discrete layer. For example, in some embodiments, bottom 406 and the transparent member 414 may be fused with different material or fused as one layer with same type of material.

The optical excitation assembly 312 can be configured to illuminate the sensing element 402. Optical excitation assembly 312 can include a light source such as a light emitting diode (LED), vertical-cavity surface-emitting lasers (VCSELs), electroluminescent (EL) devices, and the like. Optical detection assembly 314 can include a component selected from the group consisting of a photodiode, a phototransistor, a charge-coupled device (CCD), a junction field effect transistor (JFET) optical sensor, a complementary metal-oxide semiconductor (CMOS) optical sensor, an integrated photo detector integrated circuit, a light to voltage converter, and the like. Optical excitation 312 and optical detection 314 assemblies are discussed in further detail below.

Figure 5:
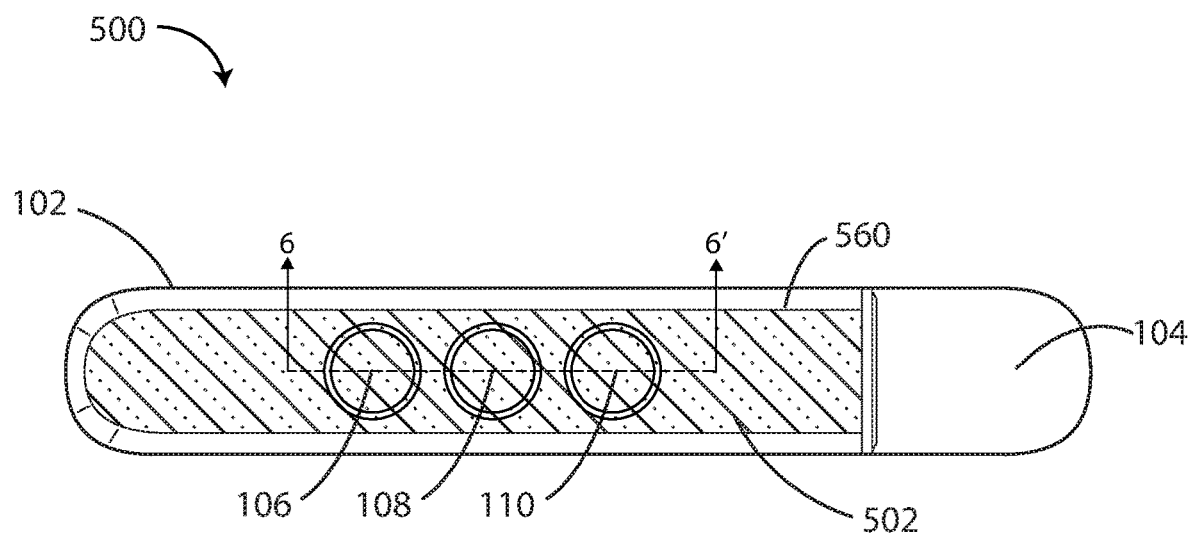
FIG. 5 is a schematic top view of an implantable medical device in accordance with additional embodiments herein.

Referring now to FIG. 5, an additional embodiment of an implantable medical device, IMB 500, is shown in accordance with the various embodiments herein. The IMB 500 can include an implantable housing 102 and a header 104 coupled to the implantable housing 102, similar to that presented in FIG. 1. Likewise, the IMD 500 can include an array of chemical sensors 106, 108, and 110 coupled to the implantable housing 102, like those shown in FIGS. 1-4. The IMD 500 can additionally include a bioerodible planarization layer 502. In some embodiments, the bioerodible planarization layer 502 can be disposed within a recessed planarization well 560.

Bioerodible planarization layer 502 can be configured to have rapid dissolution characteristics such that the planarization layer 502 maintains its integrity during implantation of the IMD 500 to protect the array of chemical sensors and masking layers during the implantation procedure. However, once the IMD 500 is in place at the implantation site, the planarization layer 502 can dissolve rapidly to reveal one or more chemical sensors to the implantation environment. As will be discussed in reference to FIG. 6, some chemical sensors protected by the planarization layer 502 may also be protected by masking layers 310, which also erode after placement of the device in vivo.

As such, both the planarization layer 502 and the masking layer(s) can be bioerodible. However, the planarization layer 502 generally erodes much faster than the masking layers. In various embodiments, the planarization layer erodes through a different mechanism than the masking layer(s). In some embodiments, the planarization layer simply dissolves after coming into contact with in the aqueous in vivo environment. In contrast, in some embodiments, the masking layer(s) must undergo a chemical reaction such as hydrolysis before erosion occurs. In other words, in some embodiments erosion of the masking layer(s) is not simply a matter of dissolution, though dissolution may be included. For example, in some embodiments, hydrolysis reactions cleave the backbone of a polymer found in the masking layer. Various other reactions can also occur to cause erosion of the masking layers.

It will be appreciated that planarization layer 502 can be configured to coat only a portion of the IMD 500, such as the array of chemical sensors 106, 108, and 110, or alternatively it can be configured to coat the entire surface area of the IMD 500. Exemplary compositions and physical properties of planarization layers are described below in more detail.

Figure 6:
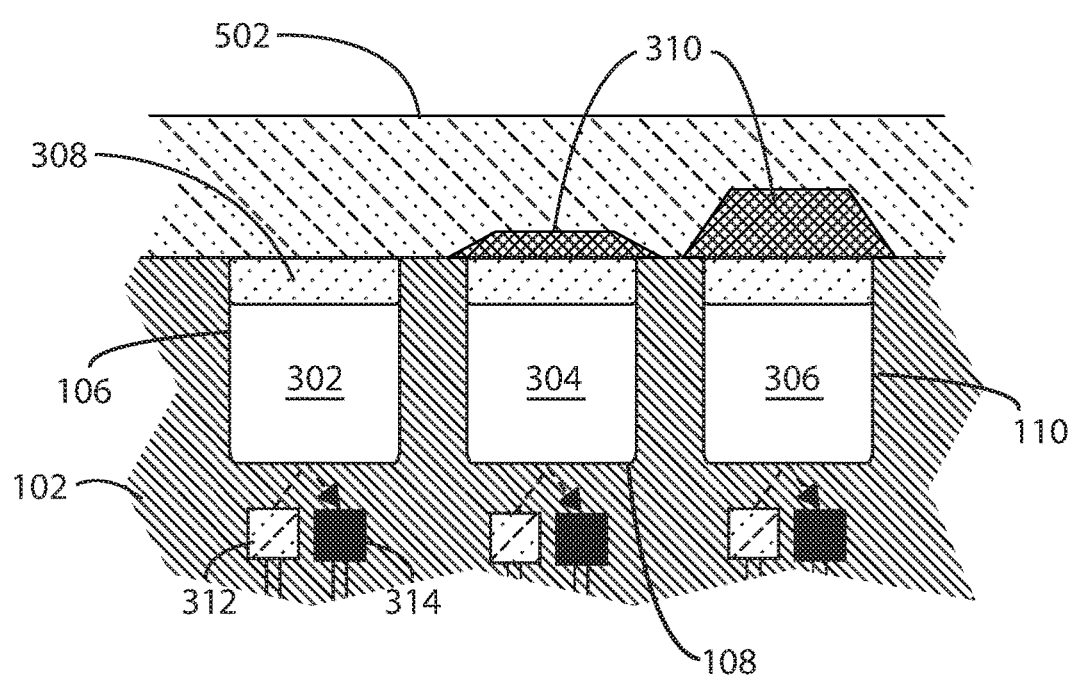
FIG. 6 is a cross-sectional view of an array of chemical sensors taken along line 6-6' of FIG. 5.

Referring now to FIG. 6, a cross-sectional view is shown of the chemical sensor array of IMD 500 as taken along line 6-6' of FIG. 5. The chemical sensor array of IMD 500 can include chemical sensors 106, 108, and 110. Each of the chemical sensors 106, 108, and 110 can include, but not be limited to, sensing elements 302, 304, and 306, respectively. Each of the chemical sensors 106, 108, and 110 can also include an analyte window 308 disposed on the top of sensing elements 302, 304, and 306. Each analyte window 308 can be formed from a permeable material, such as an ion permeable polymeric matrix material. In some embodiments, the analyte window can be created from the ion permeable polymeric matrix material, polyhydroxyethyl methacrylate (polyHEMA). In other embodiments, the analyte window can be created from other ion permeable polymeric matrix materials as discussed in more detail below.

Each chemical sensor 106, 108, and 110 can also include a bioerodible masking layer 310 disposed on the exterior surface of the analyte window 308 of one or more of the chemical sensors so as to shield the chemical sensor from the implant environment until a predetermined point in time. Masking layer 310 can be formed from bioerodible polymers including, but not limited to, polylactic acid, poly-L-lactic acid, and derivatives thereof. In some embodiments, masking layer 310 can also include an anti-inflammatory agent. In some embodiments, the anti-inflammatory agent can include ketorolac, dexamethasone, hydrocortisone, prednisolone, methylprednisolone, indomethacin, diclofenac, ketoprofen, piroxicam, metamizol magnesium and the like. In some embodiments, anti-inflammatory agents can be configured to be eluted shortly after implantation of the device. Additional masking layer materials and their physical properties suitable for use with the embodiments herein are described more fully below.

In some embodiments, each masking layer 310 can seal off a chemical sensor and therefore function to isolate the chemical sensor until degradation of the masking layer materials. The size and composition of each masking layer 310 can be as described above in reference to FIG. 3 and more fully below. In some embodiments, each masking layer 310 disposed on the exterior surface of the analyte window(s) 308 can be a different thickness. In some embodiments, the masking layer 310 disposed on the exterior surface of the analyte window(s) 308 can be the same thickness. In some embodiments, each masking layer 310 disposed on the exterior surface of the analyte window(s) 308 can be created from the same material. In some embodiments, the masking layer 310 disposed on the exterior surface of the analyte window(s) 308 can be created from different materials.

As discussed in reference to FIG. 5, the IMD 500 can also include a planarization layer 502 configured to coat only a portion of the IMD 500, such as the array of chemical sensors 106, 108, and 110, or alternatively it can be configured to coat the entire surface area of the IMD 500. The planarization layer 502 can be configured to substantially decompose within milliseconds, seconds, minutes, or hours, and immediately expose any underlying chemical sensors that do not have an additional masking layer 310 disposed thereon. The planarization layer 502 can be configured to be sufficiently thick enough to match the thickness of or cover the thickest masking layer disposed on the surface of the IMD.

In some embodiments, the planarization layer 502 can be between 50-500 μm thick. In some embodiments, the planarization layer can be between 0.5-2.0 mm thick. In some embodiments, each planarization layer can be any of the following thicknesses: 50 μm, 75 μm, 100 μm, 200 μm, 250 μm, 300 μm, 400 μm, 500 μm, 1 mm, 2 mm, or 3 mm thick. In some embodiments the thickness of the planarization layer 502 can be in a range wherein any of the foregoing thicknesses can serve as the upper or lower bound of the range, provided that the upper bound is greater than the lower bound.

Figure 7:
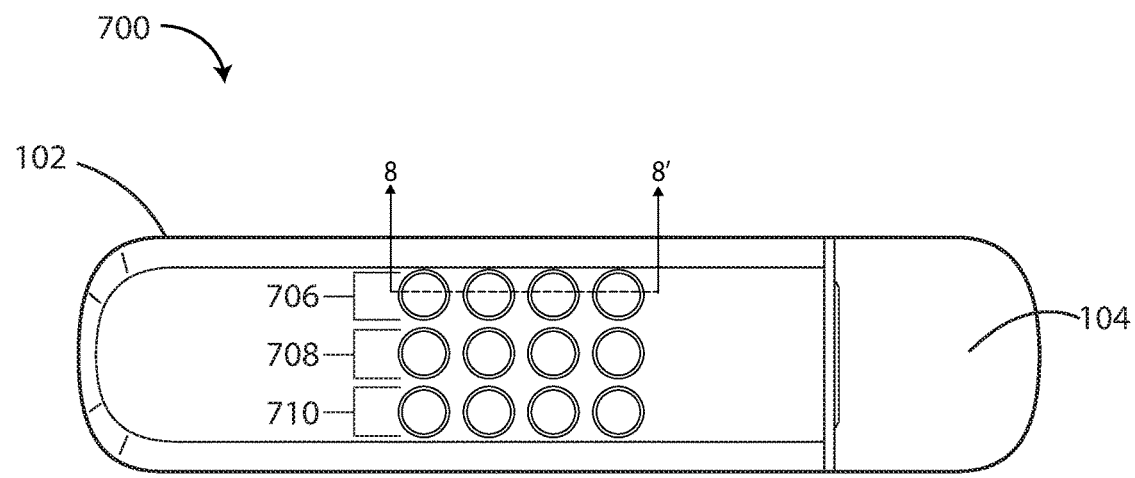
FIG. 7 is a schematic top view of an implantable medical device in accordance with additional embodiments herein.

Referring now to FIG. 7, an additional embodiment of an implantable medical device, IMB 700, is shown in accordance with the embodiments herein. The IMB 700 can include an implantable housing 102 and a header 104 coupled to the implantable housing 102, as described elsewhere herein. The IMD 700 can also include an array of three sets of chemical sensors 706, 708, and 710, where each set of chemical sensors includes four individual chemical sensors per row. In some embodiments, IMD 700 can include many sets of chemical sensors, for example, there may be 1, 2, 3, 4, 5, 6, 7, 8, 9, 10, or more sets of chemical sensors. In some embodiments, the IMD 700 can include a number of individual chemical sensors per set, including 1, 2, 3, 4, 5, 6, 7, 8, 9, 10, or more individual chemical sensors per chemical sensor set. It will be appreciated that many combinations of chemical sensor sets and individual chemical sensors per chemical sensor set can be contemplated in accordance with the embodiments herein. It will also be appreciated that the array of three sets of chemical sensors 706, 708, and 710 can be covered by a planarization layer as discussed elsewhere herein.

In the embodiment shown in FIG. 7, each individual chemical sensor of chemical sensor set 706 can be configured to detect the same analyte, such as, for example, potassium. In chemical sensor set 706, each individual sensor can be activated to detect potassium at predetermined periods in time. In some embodiments, each individual chemical sensor of chemical sensor set 706 can be activated to detect potassium at the same time. In some embodiments, each individual chemical sensor of chemical sensor set 706 can be activated to detect potassium at different points in time. In some embodiments, when one of the individual chemical sensors in chemical sensor set 706 is activated, the other three individual chemical sensors are in a state of inactivation, deactivation, or both. In some embodiments, when one individual chemical sensor in the chemical sensor set 706 is determined to need replacement, it can be deactivated and the next sensor in the set can be activated after its bioerodible masking layer has been degraded.

In some embodiments, each individual chemical sensor of chemical sensor set 708 can be configured to detect a different analyte than each individual chemical sensor of chemical sensor set 706. For example, if chemical sensor set 706 is configured to detect potassium, then chemical sensor set 708 can be configured to detect creatinine. Similarly, chemical sensor set 710 can be configured to detect an analyte different than chemical sensor set 706 and chemical sensor set 708. For example, if chemical sensor set 706 is configured to detect potassium and chemical sensor set 708 is configured to detect creatinine, then chemical sensor set 710 can be configured to detect bicarbonate ion. In some embodiments, all of the individual chemical sensors in each of the chemical sensor sets 706, 708, and 710 can be configured to detect the same analyte. It will be appreciated that many configurations can be contemplated within and across various chemical sensor sets such that many combinations of suitable analytes can be detected by the array of chemical sensor sets present on the IMD 700.

Figure 8:
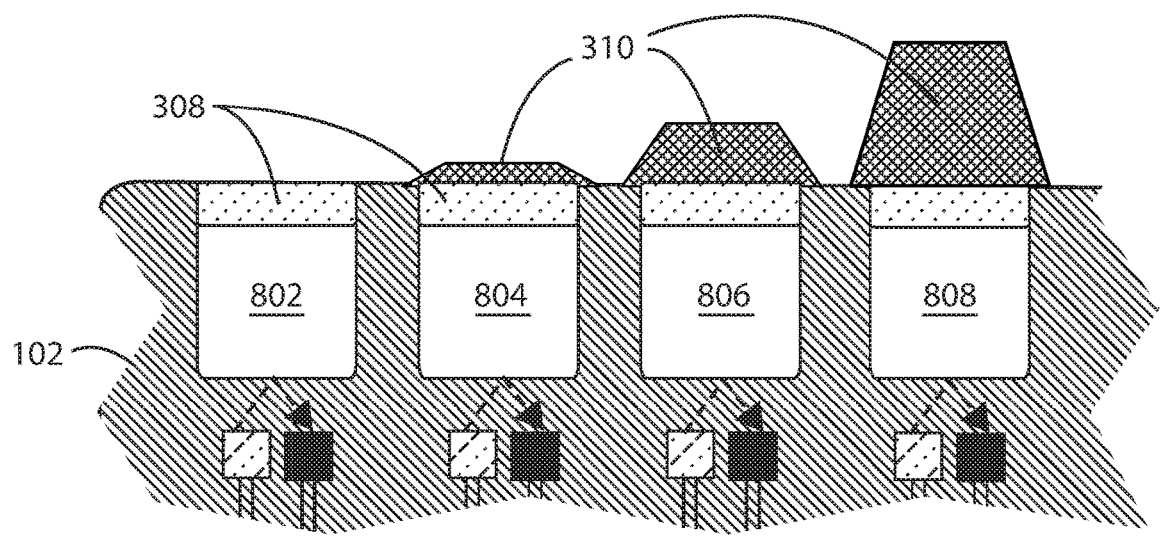
FIG. 8 is a cross-sectional view of an array of chemical sensors taken along line 8-8' of FIG. 7.

Referring now to FIG. 8, a schematic cross-sectional view of the chemical sensor set 706 of IMD 700 along line 8-8' of FIG. 7 is shown. The individual chemical sensors of chemical sensor set 706 of IMB 700 can include sensing elements 802, 804, 806, and 808. Each individual chemical sensors of chemical sensor set 706 can also include an analyte window 308 disposed on the top of sensing elements 802, 804, 806, and 808. Each analyte window 308 can be formed from a permeable material, such as an ion permeable polymeric matrix material, as discussed in more detail below.

Figure 9:
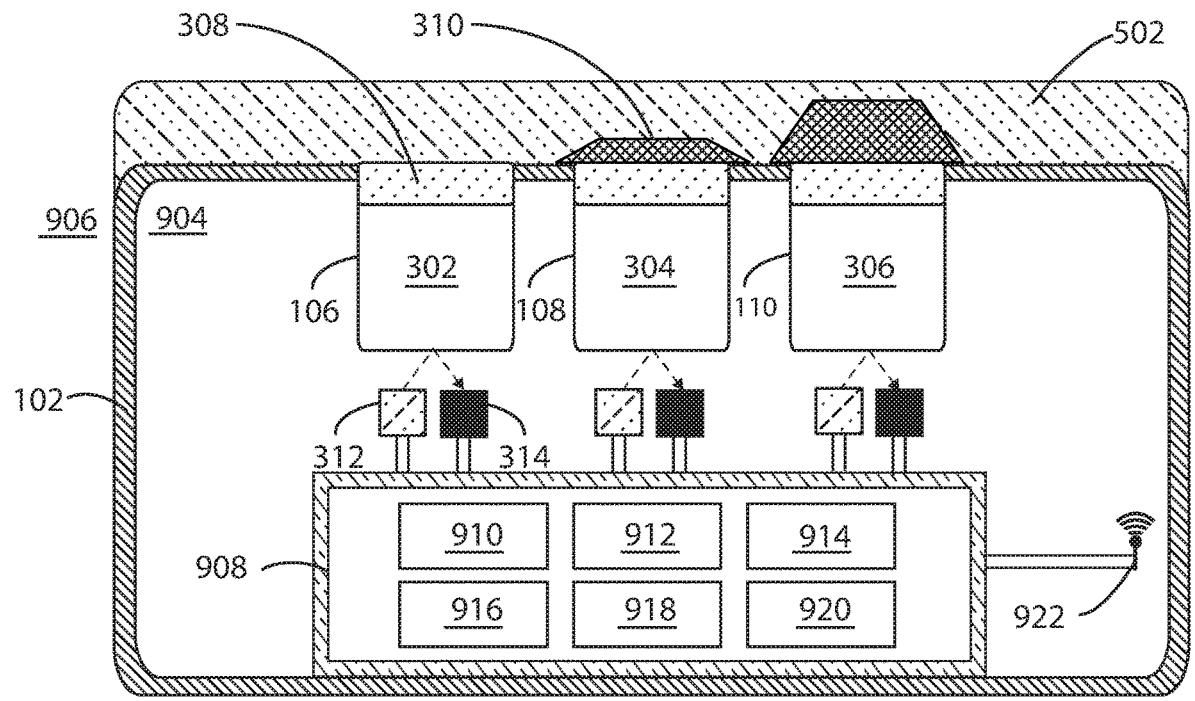
FIG. 9 is a schematic cross-sectional view of an implantable medical device in accordance with various embodiments herein.

Referring now to FIG. 9, a schematic cross-sectional view of an IMD in accordance with various embodiments herein is shown. The IMB can include implantable housing 102. The implantable housing 102 of can include various materials such as metals, polymers, ceramics, and the like. In some embodiments, the implantable housing 102 can be a single integrated unit. In other embodiments, the implantable housing 102 can include implantable housing 102 and epoxy header 104 (not shown), as discussed above. In some embodiments, the implantable housing 102, or one or more portions thereof, can be formed of titanium. In some embodiments, one or more segments of the implantable housing 102 can be hermetically sealed.

Implantable housing 102 can define an interior volume 904 that in some embodiments is hermetically sealed off from the area 906 outside of the IMD. The IMD can include circuitry 908, which can be disposed within the interior volume 904, within the header (see 104 in FIG. 1), or distributed between both. Circuitry 908 can include various components, such as components 910, 912, 914, 916, 918, and 920. In some embodiments, these components can be integrated and in other embodiments these components can be separate. In some embodiments, the components can include one or more of a microprocessor, memory circuitry (such as random access memory (RAM) and/or read only memory (ROM)), recorder circuitry, telemetry circuitry, chemical sensor interface circuitry, power supply circuitry (which can include one or more batteries), normalization circuitry, chemical sensor control circuitry, and the like. In some embodiments recorder circuitry can record the data produced by the chemical sensor and record time stamps regarding the same. In some embodiments, the circuitry can be hardwired to execute various functions, while in other embodiments the circuitry can be implemented as instructions executing on a microprocessor or other computation device.

A telemetry interface 922 can be provided for communicating with external devices such as a programmer, a home-based unit, and/or a mobile unit (e.g., a cellular phone, portable computer, etc.). In some embodiments telemetry interface 922 can be provided for communicating with implanted devices such as a therapy delivery device (e.g. a pacemaker, cardioverter-defibrillator) or monitoring-only device (e.g. an implantable loop recorder). In some embodiments, the circuitry can be implemented remotely, via either near-field, far-field, conducted, intra-body or extracorporeal communication, from instructions executing on any of the external or the implanted devices, etc. In some embodiments, the telemetry interface 922 can be located within implantable housing 102. In some embodiments, the telemetry interface 922 can be located in header 104.

The optical excitation 312 and optical detection 314 assemblies of the chemical sensors embodied herein can be in electrical communication with the circuitry 908 within the interior volume 904. In some embodiments, the control circuitry 908 can be configured to selectively activate the optical excitation 312 and optical detection 314 assemblies of the chemical sensors embodied herein. In some embodiments, the control circuitry 908 can be configured to selectively activate the optical excitation 312 and optical detection 314 assemblies of one or more chemical sensors embodied herein only after the masking layer has degraded completely. In some embodiments, the control circuitry 908 can be configured to periodically monitor one or more masked chemical sensors by activating the respective optical excitation 312 and optical detection 314 assemblies at predetermined time intervals prior to the time to monitor degradation of any particular masking layer.

Figure 10:
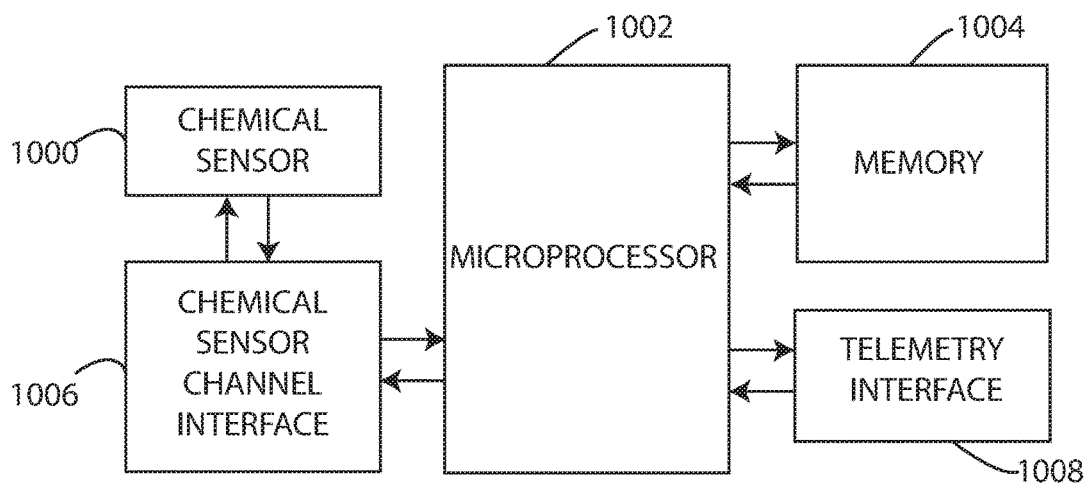
FIG. 10 is a schematic diagram of components of an implantable medical device in accordance with various embodiments herein.

Referring now to FIG. 10, a schematic diagram of components of the implantable medical devices in accordance with various embodiments herein. It will be appreciated that some embodiments can include additional elements beyond those shown in FIG. 10. In addition, some embodiments may lack some elements shown in FIG. 10. The IMD can gather information through one or more sensing channels. A microprocessor 1002 can communicate with a memory 1004 via a bidirectional data bus. The memory 1004 can include read only memory (ROM) or random access memory (RAM) for program storage and RAM for data storage, or any combination thereof. The implantable medical device can also include one or more chemical sensors 1000 and one or more chemical sensor channel interfaces 1006 which can communicate with a port of microprocessor 1002. The chemical sensor channel interface 1006 can include various components such as analog-to-digital converters for digitizing signal inputs, sensing amplifiers, registers which can be written to by the control circuitry in order to adjust the gain and threshold values for the sensing amplifiers, source drivers, modulators, demodulators, multiplexers, and the like. A telemetry interface 1008 is also provided for communicating with external devices such as a programmer, a home-based unit, and/or a mobile unit (e.g., a cellular phone, portable computer, etc.), implanted devices such as a pacemaker, cardioverter-defibrillator, loop recorder, and the like.

Masking Layer

The masking layers embodied herein can be configured to keep any number of chemical sensors in an isolated state for a predetermined period of time prior to their use. As a result, the masking layer can provide a number of beneficial features to the IMD over the lifetime of the device. For example, the masking layer can prolong the lifetime of the IMD through the sequential exposure and activation of each additional chemical sensor once the previous chemical sensor has become obsolete. Consequently, the masking layer can allow for longer term monitoring of a patient over the lifetime of the IMD. The masking layers can also eliminate the need for frequent replacement of the IMD.

The masking layers embodied herein can be created from a number of biocompatible and bioerodible materials. In some embodiments, the masking layers can be prepared from biocompatible and bioerodible polymers such as polylactic acid (PLA), poly-L-lactic acid (PLLA), poly-lactide-co-glycolide (PLGA), poly-D, L-lactide-(PDLA), polyglycolide, polyhydroxyalkanoate, polyhydroxybuterate, polycarbonate, and derivatives and copolymers thereof. In some embodiments, the masking layers can be prepared from biocompatible and bioerodible metals such as magnesium, stainless steel, iron, zinc, cobalt, tungsten, molybdenum, silver, chromium, nickel, and oxides, nitrates, or alloys thereof.

In some embodiments, the masking layer deposited on a first chemical sensor can be created by using one or more types of bioerodible material having a unique degradation rate, and the masking layer deposited on a second chemical sensor can be created by using a different type of bioerodible material, or combination thereof, to yield a second unique degradation rate, different than that of the first. It will be appreciated that any number of masking layers can be contemplated, each having its own unique composition and degradation rate associated therewith, such that each chemical sensor can be protected by a unique masking layer having a sequentially longer degradation rate than the other chemical sensors.

In some embodiments, the masking layer can be configured to degrade over a specific amount of time. In some embodiments, the masking layer can be configured to degrade over a period of minutes. In some embodiments, the masking layer can be configured to degrade over a period of hours. In some embodiments, the masking layer can be configured to degrade over a period of days. In some embodiments, the masking layer can be configured to degrade over a period of months. In some embodiments, the masking layer can be configured to degrade over a period of years.

In some embodiments, the masking layer can be configured to degrade over a period of time including 1, 2, 3, 4, 5, 10, 15, 20, 25, or 30 days. In some embodiments, the masking layer can be configured to degrade over a period of time including 1, 2, 3, 4, 5, 6, 7, 8, 9, 10, 11, or 12 months. In some embodiments, the masking layer can be configured to degrade over a period of time including 1, 2, 3, 4, or 5 years. In some embodiments the time period for degradation of the masking layer can independently be in a range wherein any of the foregoing times can serve as the upper or lower bound of the range, provided that the upper bound is greater than the lower bound.

In some embodiments, the masking layer can be made of a material such that it exhibits surface erosion characteristics. Surface erosion can occur when a material, such as a polymer, degrades from the exterior surface inward. Thus, the material continually sheds the exterior surface over a period of time until the material is completely degraded. In other embodiments, the masking layer can be made of a material such that it exhibits bulk erosion characteristics. Bulk erosion can occur when a material degrades uniformly throughout the material until the material is completely degraded. In some embodiments, the masking layer can be degraded through the process of hydrolysis. In some embodiments, the masking layer can be degraded through dissolution. In some embodiments, the masking layer can be degraded by changes in the local pH surrounding the masking layer. In some embodiments, the masking layer can be degraded by photolysis. In some embodiments, each masking layer can be degraded by applying an electrical current to the masking layer if it is created from a metal or metal alloy.

It will be appreciated that a masking layer can have a degradation rate that is dependent not only the thickness of the masking layer, but also on the material composition of the masking layer. Thus, for example, two masking layers having the same thickness but different material compositions may exhibit markedly different degradation rates based on the material composition of each masking layer. Similarly, two masking layers having different thicknesses, but the same material composition, may exhibit markedly different degradation rates based on the thickness of each masking layer. It will be appreciated that many masking layers having unique compositions and/or thicknesses, and thus unique degradation rate, may be utilized in the spirit and scope of the embodiments herein.

In some embodiments, the masking layers embodied herein can contain additional additives. In some embodiments, the masking layers can include an active therapeutic agent such as an anti-inflammatory agent. In some embodiments, the anti-inflammatory agent can include a corticosteroid, such as dexamethasone. In some embodiments, the anti-inflammatory agent can include, but not be limited to, ketorolac, dexamethasone, hydrocortisone, prednisolone, methylprednisolone, indomethacin, diclofenac, ketoprofen, piroxicam, metamizol magnesium, and the like.

Planarization Layer

The planarization layers embodied herein can be configured to protect the underlying masking layers and chemical sensors during implantation. The planarization layers embodied herein can be created from a number of biocompatible and bioerodible materials with rapid erosion properties. For example, the planarization layer can be created from any number of sugars, including but not limited to sucrose, dextrose, glucose, fructose, lactose, mannitol, mannose, hydroxypropyl cellulose, hydroxypropyl ethyl cellulose, hydroxypropyl methylcellulose, microcrystalline cellulose, polyvinyl alcohol, ethylcellulose, polyethylene glycol (PEG), and the like. In some embodiments, the planarization layer can be made from an agglomerated material (e.g., can be an agglomerate).

Once the IMB is in place at the implantation site, the planarization layer can erode away within a predetermined amount of time after implantation. In some embodiments, the planarization layer can be configured to degrade almost instantaneously. In some embodiments, the planarization layer can be configured to degrade within 50 ms, 75 ms, 100 ms, 250 ms, 500 ms, 750 ms, 1 s, 10 s, 15 s, 30 s, 45 s, 1 min, 5 min, 10 min, 15 min, 20 min, 25 min, 30 min, 35 min, 40 min, 45 min, 50 min, 55 min, 1 hr, 2 hr, 3 hr, 4 hr, 5 hr, 6 hr, 7 hr, 8 hr, 9 hr, 10 hr, 11 hr, or 12 hr. In some embodiments the time period for erosion of the planarization layer can independently be in a range wherein any of the foregoing times can serve as the upper or lower bound of the range, provided that the upper bound is greater than the lower bound.

In some embodiments, each planarization layer can be any of the following thicknesses: 50 µm, 75 µm, 100 µm, 200 µm, 250 µm, 300 µm, 400 µm, 500 µm, 1 mm, 2 mm, or 3 mm thick. In some embodiments the thickness of each planarization layer can independently be in a range wherein any of the foregoing thicknesses can serve as the upper or lower bound of the range, provided that the upper bound is greater than the lower bound. In some embodiments, the planarization layer can be between 50-500 µm thick. In some embodiments, the planarization layer can be between 0.5-2.0 mm thick.

In some embodiments, the planarization can be sufficiently thick to cover any number of masking layers with the same or varying thicknesses. In some embodiments, the planarization layer can be configured to coat only the chemical sensors. In other embodiments, the planarization layer can be configured to coat the entire IMD or a planarization well thereon. In embodiments where one or more masking layers are of varying thicknesses, it will be appreciated that the planarization layer will similarly vary in thickness in regions disposed on the surface of the masking layers.

Sensor Operational States and Calibration

In some embodiments, prior to implantation, each sensing element of each chemical sensor can be permeated with a solution having a physiological analyte of interest at a known concentration (at greater than physiologic concentrations, at physiological concentrations, or at less than physiologic concentrations). Various physiological analytes suitable for use in the chemical sensors herein are described more fully below.

While not intending to be bound by theory, if the sensing element (prior to implantation) is permeated with a non-physiological concentration of an analyte (so much greater than physiologic or so much less than physiologic that the values are physiologically impossible to have occurred naturally in the patient) then assessing when the sensing element begins reporting a physiologically possible concentration allows a determination to be made of when the sensor has become partially exposed (because partial exposure allows for diffusion to equalize the concentration of the analyte in the sensing element with the surrounding tissue).

For example, one or more chemical sensors embodied herein can include a sensing element permeated by a solution of about 5, 6, 7, 8, 9, 10, 11, 12, 13, 14, 15, 20, 25, 30 mM or more potassium (or a concentration of potassium that falls within a range between any of the foregoing), all of which are above the normal physiological range for potassium. A physiological potassium concentration can typically be in the range from about 3.5-5.0 mM. Concentrations of potassium above 10 mM (for example) would not be physiologically possible in blood, interstitial fluid, or serum under most circumstances.

In some embodiments, prior to implantation, each sensing element of each chemical sensor can be permeated with a solution containing an optical dye (or other diffusible compound that absorbs light at one or more wavelengths) that interferes with optical sensing of the sensing element. Optical dyes can be selected depending on the specific wavelengths of desired interference. Exemplary optical dyes can include those that are biocompatible. Optical dyes can include, but are not limited to, cyanine, indocyanine, fluorescein, cytate, cybesin, and the like. When the sensor becomes partially exposed, then this optical dye can diffuse out of the sensing element and will therefore stop interfering with optical sensing of the sensing element. As such, in these types of embodiments, sensing the lack of interference from the optical dye can be used as an indication that the sensing element has become partially exposed.

Fully Sealed Sensors

Sensor elements that are totally sealed off from the in vivo environment will (if interrogated with an optical excitation device or assembly) indicate a concentration that matches whatever the known concentration of that analyte was in the solution which was originally placed into the well with the sensor element. Sealed off sensors will not reflect the actual concentrations of analytes in the in vivo environment around the implanted device nor will they reflect changes in those actual concentrations. As such, they can, in some embodiments, be periodically interrogated either as a control (because the concentration value is known) or as a test to see if the masking layer has eroded enough to start to allow some diffusion of analytes into and out of the sensing element. In embodiments that include a planarization layer, the planarization could also, albeit briefly, contribute to a chemical sensor being fully sealed.

Partially Exposed Sensors

As a masking layer is eroded away, there will come a point where a diffusion path opens up which will allow diffusion to occur and the concentration of analyte in the now partially exposed sensor element will gradually match the amount of potassium in the tissues around the implanted device. Thus, concentration values reported by a partially exposed sensor can reflect actual physiological values.

However, if the masking layer still partially blocks the sensor, then diffusion will be limited and the response time will be slower than an otherwise similar chemical sensor that is not partially blocked by a masking layer (e.g., is fully exposed). In embodiments that include a planarization layer, the planarization could also, albeit briefly, contribute to a chemical sensor being partially exposed.

Fully Exposed Sensors

In some embodiments, when an IMB is implanted into the body, any chemical sensors not protected by a masking layer and/or planarization layer can be activated essentially immediately upon implantation. Through passive diffusion of analytes into and out of the sensor element, the concentration of analyte in the unmasked sensor element will quickly match the amount of potassium in the tissues around the implanted device and provide concentrations readings reflective of analyte concentrations in the tissue into which the device is implanted.

Further, because diffusion into and out of the sensor element is not obstructed, the response time (e.g., time in which it takes the sensor to reflect a change in concentration of an analyte that has occurred in the in vivo environment) will be relatively fast compared with a partially blocked chemical sensor.

Some key aspects of sensors in these three different functional statuses are summarized in table 1 below.

|  | Fully Sealed | Partially Exposed | Fully Exposed |
| --- | --- | --- | --- |
| Concentration of Analyte in Sensing Element | 7.0 mM K$^{+}$* | Physiologic Concentration | Physiologic Concentration |
| Response Time of Sensor | NA | Long | Short |

*It will be appreciated that K+ is merely one example of an analyte and many different analytes are contemplated herein; further 7.0 mM is just one exemplary concentration and that many different specific concentrations of analytes are contemplated herein.

Before relying upon the concentration data produced by a particular chemical sensor the implanted medical device (or another device in communication with the implanted medical device) can evaluate the data to determine if the sensor if fully exposed. In some embodiments, the implanted medical device can include a detector unit comprising a processor (such as a microprocessor, microcontroller, application specific integrated circuit, or the like) and the detector unit can be configured to monitor an operational status of the at least first chemical sensor and second chemical sensor.

In some embodiments, the detector unit is configured to compare the operational status of the first chemical sensor to the operational status of the second chemical sensor. In some embodiments, the detector unit is configured to periodically evaluate the second chemical sensor status to monitor the sensed concentration of the analyte in order to assess the erosion status of the first bioerodible masking layer. In some embodiments, the detector unit is configured to calculate the response time of the first sensor and the response time of the second sensor and compare the two response times. In some embodiments, the detector determines that the second sensor is ready for active use (e.g., the data produced thereby can be used and relied upon) when the concentration of the analyte sensed by the second chemical sensor status falls to physiological levels and the response time of the second sensor is within some threshold value of the response time of the second sensor. For example, when the response time of the second sensor is within 100%, 80%, 60%, 40%, 30%, 20%, 10%, or less of the response time of the first sensor (or previously active sensor). In some embodiments, the detector unit is configured to disable the first chemical sensor (or previously used chemical sensor) when it is determined that another chemical sensor (or second chemical sensor) is ready for active use. Disabling can include various steps such as one or more of no longer activating an optical excitation device or assembly for the disabled chemical sensor and discarding data produced by the disabled chemical sensor.

In some embodiments, the degradation process of the masking layer can be periodically monitored by selectively activating the optical excitation and detection assemblies for a chemical sensor and recording the output for that chemical sensor. In some embodiments, tracking the response time of a particular chemical sensor over time can be used to predict when that particular chemical sensor may be capable of being fully activated. For example, if it has been observed that a particular chemical sensor has a response time that is dropping by a certain amount or percent each day and it currently has a response time that is a certain fixed value or percent different than a previously relied upon chemical sensor, then the amount of time for the response times of the two chemical sensor to become approximately equal can be estimated through extrapolation, assuming linear or nonlinear change over time.

It will be appreciated that if at any time the chemical sensor reports a signal that is greater than the original concentration of the analyte solution (assuming the sensor is fully sealed), or completely out of physiological range (assuming the sensor is fully exposed), that sensor can be flagged for further analysis, or it can be disabled or deactivated, among other interventions.

In some embodiments, absolute values of a physiological analyte can be used to calibrate or otherwise test the accuracy of concentration values derived from data produced by a chemical sensor. For example, a blood sample can be collected from a patient around the time when a chemical sensor is expected to be fully exposed or thereafter. The concentration of the physiological analyte as determined by in vitro analysis of the blood sample can then be compared against the concentration of that analyte as reported by the particular chemical sensor. If the values match, it can be assumed that the chemical sensor is accurate and can be relied upon, assuming that its response times are also on par with previous sensors. However, if the values do not match and this difference is stable, then it can be assumed that the sensor may need to be calibrated and/or adjusted. In another example, analyte concentrations as reported by a previously calibrated and accurate chemical sensor can be used alone, or in conjunction with the data obtained from the blood sample analysis, to provide an absolute value for a physiological analyte.

In some embodiments, the IMD can be configured to perform automated chemical sensor fault correction procedure when one or more chemical sensors stably reports higher or lower concentrations of a physiological analyte than expected. For example, a chemical sensor may reach a fully normal response time (e.g., comparable to other sensors previously active), yet the concentration of analyte reported by that chemical sensor remains higher or lower than expected or empirically determined physiological levels. In such a case, a step-change error correction procedure or similar error correction procedure can be triggered by the IMD. In some embodiments, the IMD can trigger an alert to indicate that the patient must go to the medical clinic for a blood draw to compare the absolute value of the physiological analyte to the value reported by the chemical sensor for purposes of calibration or error correction. In some embodiments, the IMD can use data from the previous chemical sensor for error correction if it has been determined that the previous chemical sensor was recently calibrated and accurately reporting concentrations of the physiological analyte. In various embodiments, the suspect chemical sensor can be corrected by applying an offset to get the chemical sensor to report the value as obtained during the blood sample analysis or as obtained from the previous chemical sensor.

Chemical Sensors

Chemical sensors herein can be of various types. In some embodiments, the physiological concentration of an analyte is sensed directly. In other embodiments, the physiological concentration of an analyte is sensed indirectly. By way of example, a metabolite of a particular analyte can be sensed instead of the particular analyte itself. In other embodiments, an analyte can be chemically converted into another form in order to make the process of detection easier. By way of example, an enzyme can be used to convert an analyte into another compound that is easier to detect. For example, the hydrolysis of creatinine into ammonia and N-methylhydantoin can be catalyzed by creatinine deiminase and the resulting ammonia can be detected by a chemical sensor. In some embodiments, chemical sensors herein can include at least two functional elements: a receptor and a transducer. It will be appreciated that other elements can also be included. The receptor part of a chemical sensor can transform chemical information into a form of energy or signal that can be measured by the transducer. The transducer can transform and/or convey the energy or signal carrying the chemical information so as to provide a useful analytical signal.

Chemical sensors can include optical devices that utilize changes of optical phenomena or properties, which are the result of an interaction of the analyte with the receptor part of the sensor. Such optical properties can include: absorbance, caused by the absorptivity of the analyte itself or by a reaction with some suitable indicator; reflectance, using a bodily component, tissue, or fluid, or using an immobilized indicator; luminescence, based on the measurement of the intensity of light emitted by a chemical reaction in the receptor system; fluorescence, measured as the positive emission effect caused by irradiation or selective quenching of fluorescence; refractive index, measured as the result of a change in solution composition, in some cases including surface plasmon resonance effects; optothermal effects, based on a measurement of the thermal effect caused by light absorption; light scattering; or the like. In some embodiments, optical chemical sensors can include an optode.

Chemical sensors can also include electrochemical devices that transform the effect of the electrochemical interaction between an analyte and an electrode into a useful signal. Such sensors can include voltammetric sensors, including amperometric devices. Also included are sensors based on chemically inert electrodes, chemically active electrodes and modified electrodes. Also included are sensors with and without (galvanic sensors) a current source. Sensors can also include potentiometric sensors, in which the potential of the indicator electrode (ion-selective electrode, redox electrode, metal oxide electrode, or the like) is measured against a reference electrode. Sensors can include chemically sensitized field effect transistors (CHEMFET) in which the effect of the interaction between the analyte and the active coating is transformed into a change of the source-drain current. Sensors can include potentiometric solid electrolyte gas sensors.

Chemical sensors can also include electrical devices based on measurements, where no electrochemical processes take place, but the signal arises from the change of electrical properties caused by interaction with the analyte. Such sensors can include metal oxide semiconductor sensors based on reversible redox processes of analyte gas components, organic semiconductor sensors, based on the formation of charge transfer complexes, which modify the charge carrier density, electrolytic conductivity sensors, and electric permittivity sensors.

Chemical sensors can also include mass sensitive devices that transform the mass change at a specially modified surface into a change of a property of the support material. The mass change can be caused by accumulation of the analyte. Such sensors can include piezoelectric devices based on the measurement the frequency change of the quartz oscillator plate caused by adsorption of a mass of the analyte at the oscillator and surface acoustic wave devices that depend on the modification of the propagation velocity of a generated acoustical wave affected by the deposition of a definite mass of the analyte.

Chemical sensors can also include magnetic devices based on the change of paramagnetic properties of a gas being analyzed. Chemical sensors can also include thermometric devices based on the measurement of the heat effects of a specific chemical reaction or adsorption that involves the analyte.

In one example of the operation of an optical chemical sensor, analytes of interest from the in vivo environment can diffuse into a chemical sensing element causing a detectable change in the optical properties of the chemical sensing element. Light can be generated by an optical excitation device or emitter, such as an LED or similar device, and can pass through the optical window and into the chemical sensing element. Light can then either be preferentially reflected from or re-emitted by the chemical sensing element proportionally to the sensed analyte and pass back through the optical window before being received by a light detection device or receiver, such as a charge-coupled device (CCD), a photodiode, a junction field effect transistor (JFET) type optical sensor, of complementary metal-oxide semiconductor (CMOS) type optical sensor. Various aspects of exemplary chemical sensors are described in greater detail in U.S. Pat. No. 7,809,441, the content of which is herein incorporated by reference in its entirety. In another example of the operation of an optical chemical sensor, the optical properties of a tissue or fluid in the body can be directly analyzed. By way of example, light can be generated by an optical excitation device that can be delivered to a component, tissue, or fluid in the body and a light detection device can be used to sense an optical property of the light that has interfaced with the component, tissue, or fluid.

Ion-Selective Sensors

In accordance with the embodiments herein, sensing element(s) can include one or more ion-selective sensors. Ion-selective sensors may either rely on surface phenomena or on concentration changes inside the bulk of a phase. Ion-selective sensors can include optical sensors, including both non-carrier optical sensors and carrier-based optical sensors, and ion-selective electrodes (ISEs). In some embodiments, the ion-selective sensor is fluorimetric, and can include a complexing moiety and a fluorescing moiety. Fluorimetric ion-selective sensors can exhibit differential fluorescent intensity based upon the complexing of an analyte to a complexing moiety. In some embodiments, the ion-selective sensor can be colorimetric, and can include a complexing moiety and a colorimetric moiety. Colorimetric ion-selective sensors can exhibit differential light absorbance based upon the complexing of an analyte to a complexing moiety.

In some embodiments, the ion-selective sensor comprises a non-carrier or carrier-based fluorescent or colorimetric ionophoric composition that comprises a complexing moiety for reversibly binding an ion to be analyzed, and a fluorescing or colorimetric moiety that changes its optical properties as the complexing agent binds or releases the ion. The complexing agents of the invention can optionally be appended with one or more organic substituents chosen to confer desired properties useful in formulating the ion sensing composition. By way of example, the substituents can be selected to stabilize the complexing agent with respect to leaching into the solution to be sensed, for example, by incorporating a hydrophobic or polymeric tail or by providing a means for covalent attachment of the complexing agent to a polymer support within the ion-selective sensor.

In some embodiments, the sensing element can include ion-selective sensors such as an ionophore or a fluoroionophore. Suitable ionophores for use with the embodiments herein can include, but not be limited to, sodium specific ionophores, potassium specific ionophores, calcium specific ionophores, magnesium specific ionophores, and lithium specific ionophores. Suitable fluoroionophores for use with the embodiments herein can include, but not be limited to, lithium specific fluoroionophores, sodium specific fluoroionophores, and potassium specific fluoroionophores.

Exemplary ion-selective sensors and methods for their use are disclosed in commonly assigned U.S. Pat. No. 7,809,441, the contents of which is herein incorporated by reference in its entirety.

Optical Excitation and Detection Assemblies

In some embodiments, the optical excitation assembly 312 can include solid state light sources such as GaAs, GaAlAs, GaAlAsP, GaAlP, GaAsP, GaP, GaN, InGaAlP, InGaN, ZnSe, or SiC light emitting diodes or laser diodes that excite the sensing element(s) at or near the wavelength of maximum absorption for a time sufficient to emit a return signal. However, it will be understood that in some embodiments the wavelength of maximum absorption/reflection varies as a function of concentration in the colorimetric sensor.

In some embodiments, the optical excitation assembly 312 can include other light emitting components including incandescent components. In some embodiments, the optical excitation assembly 312 can include a waveguide. The optical excitation assembly 312 can also include one or more bandpass filters, high pass filter, low pass filter, antireflection elements, and/or focusing optics.

In some embodiments, the optical excitation assembly 312 can include a plurality of LEDs with bandpass filters, each of the LED-filter combinations emitting at a different center frequency. According to various embodiments, the LEDs can operate at different center-frequencies, sequentially turning on and off during a measurement, illuminating the sensing element(s). As multiple different center-frequency measurements are made sequentially, a single unfiltered detector can be used in some embodiments. However, in some embodiments, a polychromatic source can be used with multiple detectors that are each bandpass filtered to a particular center frequency.

The sensing element(s) can include one or more types of indicator beads having embedded therein various types of ion-selective sensors. Physiological analytes of interest can diffuse into and out of the sensing element(s) and bind with an ion-selective sensor to result in a fluorimetric or colorimetric response. Reference analytes can similarly diffuse into and out of the sensing element(s) and serve as a control sample. Exemplary ion-selective sensors are described more fully below.

The optical detection assembly 314 can be configured to receive light from the sensing element(s). In an embodiment, the optical detection assembly 314 can include a component to receive light. By way of example, in some embodiments, the optical detection assembly 314 can include a charge-coupled device (CCD). In other embodiments, the optical detection assembly 314 can include a photodiode, a junction field effect transistor (JFET) type optical sensor, or a complementary metal-oxide semiconductor (CMOS) type optical sensor. In some embodiments, the optical detection assembly 314 can include an array of optical sensing components. In some embodiments, the optical detection assembly 314 can include a waveguide. The optical detection assembly 314 can also include one or more bandpass filters and/or focusing optics. In some embodiments, the optical detection assembly 314 can include one or more photodiode detectors, each with an optical bandpass filter tuned to a specific wavelength range.

The optical excitation and detection assemblies embodied herein, can be integrated using bifurcated fiber-optics that direct excitation light from a light source to one or more sensing element(s), or simultaneously to sensing element(s) and a reference channel. Return fibers can direct emission signals from the sensing element(s) and the reference channels to one or more optical detection assemblies 314 for analysis by a processor, such as a microprocessor. In some embodiments, the optical excitation and optical detection assemblies are integrated using a beam-splitter assembly and focusing optical lenses that direct excitation light from a light source to the sensing element and direct emitted or reflected light from the sensing element to an optical detector for analysis by a processor.

Ion-Permeable Polymeric Matrix Materials

As referenced above, the analyte window 308 and outer barrier layer 404 of each sensing element can be formed of an ion-permeable polymeric matrix material in some embodiments. Suitable polymers for use as the ion-permeable polymeric matrix material can include, but not be limited to polymers forming a hydrogel. Hydrogels herein can include homopolymeric hydrogels, copolymeric hydrogels, and multipolymer interpenetrating polymeric hydrogels. Hydrogels herein can specifically include nonionic hydrogels. In some embodiments, hydrogels herein can be prepared from polymerization of various monomers or macromers including one or more of 2-hydroxyethyl methacrylate (HEMA), 2-hydroxypropyl methacrylate (HPMA), acrylamide, acrylic acid, N-isopropylacrylamide (NIPAm), methoxyl polyethylene glycol monoacrylate (PEGMA), and the like. In some embodiments, polymers can include, but are not limited to polyhydroxyethyl methacrylate (polyHEMA), cellulose, polyvinyl alcohol, dextran, polyacrylamides, polyhydroxyalkyl acrylates, polyvinyl pyrrolidones, and mixtures and copolymers thereof. In some embodiments, suitable polymers for use with the ion-permeable polymeric matrix described herein include those that are transparent.

Physiological Analytes

Examples of physiological analytes that can be measured in accordance with chemical sensors of embodiments herein can include, but are not limited to, electrolytes, hormones, proteins, sugars, metabolites, and the like.

Chemical sensors herein can be directed at a specific analyte or a plurality of different analytes. In an embodiment, the analyte sensed is one or more analytes relevant to cardiac health. In an embodiment, the analyte sensed is one or more analytes indicative of renal health. The analyte sensed can be an ion or a non-ion. The analyte sensed can be a cation or an anion. Specific examples of analytes that can be sensed include acetic acid (acetate), aconitic acid (aconitate), ammonium, blood urea nitrogen (BUN), B-type natriuretic peptide (BNP), bromate, calcium, carbon dioxide, cardiac specific troponin, chloride, choline, citric acid (citrate), cortisol, copper, creatinine, creatinine kinase, fluoride, formic acid (formate), glucose, hydronium ion, isocitrate, lactic acid (lactate), lithium, magnesium, maleic acid (maleate), malonic acid (malonate), myoglobin, nitrate, nitric-oxide, oxalic acid (oxalate), oxygen, phosphate, phthalate, potassium, pyruvic acid (pyruvate), selenite, sodium, sulfate, urea, uric acid, and zinc. Inorganic cations sensed by this method include but not limited to hydronium ion, lithium ion, sodium ion, potassium ion, magnesium ion, calcium ion, silver ion, zinc ion, mercury ion, lead ion and ammonium ion. Inorganic anions sensed by this method include but not limited to carbonate anion, nitrate anion, sulfite anion, chloride anion and iodide anion. Organic cations sensed by this method include but are not limited to norephedrine, ephedrine, amphetamine, procaine, prilocaine, lidocaine, bupivacaine, lignocaine, creatinine and protamine. Organic anions sensed by this method include but not limited to salicylate, phthalate, maleate, and heparin. Neutral analytes sensed by this method include but not limited to ammonia, ethanol, and organic amines. In an embodiment, ions that can be sensed include potassium, sodium, chloride, calcium, and hydronium (pH). In a particular embodiment, concentrations of both sodium and potassium are measured. In another embodiment, concentrations of both magnesium and potassium are measured.

In some embodiments, the analytes can specifically include one or more of sodium ion, magnesium ion, chloride ion, calcium ion, carbonate ion, phosphate ion, sulfate ion, insulin, aldosterone, troponin, glucose, creatinine, and BNP.

In some embodiments, the analytes can specifically include one or more of partial pressure of oxygen ($PaO_2$), partial pressure of carbon dioxide ($PaCO_2$) and oxygen saturation ($O_2Sat$).

The embodiments described herein are not intended to be exhaustive or to limit the invention to the precise forms disclosed in the following detailed description. Rather, the embodiments are chosen and described so that others skilled in the art can appreciate and understand the principles and practices. As such, while aspects have been described with reference to various specific and preferred embodiments and techniques, it should be understood that many variations and modifications may be made while remaining within the spirit and scope herein.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention claimed is:

1. An implantable medical device comprising:
   a substrate defining wells;
   a first chemical sensor and a second chemical sensor disposed within separate wells of the substrate; the first chemical sensor and the second chemical sensor configured to detect one or more analytes;
   a first bioerodible masking layer disposed over the second chemical sensor and sealing off the second chemical sensor, the first bioerodible masking layer comprising a first material having a first erosion rate;
   a protective planarization layer disposed over at least one of the first chemical sensor and the second chemical sensor such that the outermost surface of the medical device over the first sensor is flush with the outermost surface of the medical device over the second sensor; the planarization layer comprising
      a second material having an erosion rate that is faster than the erosion rate of the first bioerodible masking layer; and a solution having a greater than 5 mM concentration of potassium, wherein the solution permeates the second chemical sensor and is sealed in by the first bioerodible masking layer prior to implantation;

wherein the second chemical sensor is configured to detect potassium.

2. The implantable medical device of claim 1, each of the first chemical sensor and second chemical sensor comprising a sensing element and an analyte window disposed on the top of the sensing element.

3. The implantable medical device of claim 2, the analyte window comprising a hydrophilic polymer.

4. The implantable medical device of claim 2, the analyte window comprising polyhydroxyethyl methacrylate (poly-HEMA).

5. The implantable medical device of claim 1, wherein the first sensor becomes exposed to an in vivo environment after erosion of the protective planarization layer, but the second sensor remains isolated from the in vivo environment because of the first bioerodible masking layer.

6. The implantable medical device of claim 1, wherein the first chemical sensor is configured to be active more quickly after implantation of the implantable medical device into a patient than the second chemical sensor.

7. The implantable medical device of claim 1, further comprising a solution containing an optical dye, wherein the solution permeates the second chemical sensor and is sealed in by the first bioerodible masking layer.

8. The implantable medical device of claim 1, further comprising a third chemical sensor, wherein a second bioerodible masking layer is disposed over the third chemical sensor, the second bioerodible masking layer comprising a third material having an erosion rate that is different that the erosion rate of the first bioerodible masking layer.

9. The implantable medical device of claim 8, wherein the erosion rate of the first bioerodible masking layer is faster than erosion rate of the second bioerodible masking layer.

10. The implantable medical device of claim 8, the first and second bioerodible masking layers comprising one or more of polylactic acid (PLA), poly-L-lactic acid (PLLA), poly-lactide-co-glycolide (PLGA), poly-D, L-lactide-(PDLA), polyglycolide, polyhydroxyalkanoate, polyhydroxyburerate, or polycarbonate.

11. The implantable medical device of claim 1, further comprising a third chemical sensor, wherein a second bioerodible masking layer is disposed over the third chemical sensor, wherein the second bioerodible masking layer is thicker than the first bioerodible masking layer.

12. The implantable medical device of claim 1, the planarization layer comprising a material selected from the group consisting of an agglomerated material, a sugar, hydroxypropyl ethyl cellulose and hydroxypropyl methylcellulose.

13. The implantable medical device of claim 1, wherein the implantable medical device is configured to disable the second chemical sensor if the second chemical sensor detects a concentration of one or more analytes that is greater than the concentration of the solution.

14. An implantable medical device comprising:
a substrate defining wells;
a first chemical sensor and a second chemical sensor disposed within separate wells of the substrate; the first chemical sensor and the second chemical sensor configured to detect one or more analytes;
a first bioerodible masking layer disposed over the second chemical sensor and sealing off the second chemical sensor, the first bioerodible masking layer comprising a first material having a first erosion rate;
a protective planarization layer disposed over at least one of the first chemical sensor and the second chemical sensor such that the outermost surface of the medical device over the first sensor is flush with the outermost surface of the medical device over the second sensor; the planarization layer comprising
a second material having an erosion rate that is faster than the erosion rate of the first bioerodible masking layer; and
a solution having a greater than physiologic concentration of one or more analytes, the second chemical sensor configured to detect the one or more analytes, wherein the solution permeates the second chemical sensor and is sealed in by the first bioerodible masking layer prior to implantation.

* * * * *